United States Patent
Whitman et al.

(10) Patent No.: US 11,319,577 B2
(45) Date of Patent: *May 3, 2022

(54) CHIMERIC PRIMERS WITH HAIRPIN CONFORMATIONS AND METHODS OF USING SAME

(71) Applicant: LUMINEX CORPORATION, Austin, TX (US)

(72) Inventors: Douglas F. Whitman, Round Rock, TX (US); Hongwei Zhang, Toronto (CA)

(73) Assignee: LUMINEX CORPORATION, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/750,319

(22) Filed: Jan. 23, 2020

(65) Prior Publication Data

US 2020/0149093 A1 May 14, 2020

Related U.S. Application Data

(60) Continuation of application No. 14/270,785, filed on May 6, 2014, now Pat. No. 10,577,647, which is a division of application No. 12/826,189, filed on Jun. 29, 2010, now Pat. No. 9,587,270.

(60) Provisional application No. 61/221,271, filed on Jun. 29, 2009.

(51) Int. Cl.
| | | |
|---|---|---|
| *C12Q 1/68* | (2018.01) | |
| *C12Q 1/6818* | (2018.01) | |
| *C12Q 1/6876* | (2018.01) | |
| *C12Q 1/6853* | (2018.01) | |
| *C12Q 1/6816* | (2018.01) | |
| *C12Q 1/6823* | (2018.01) | |
| *C12Q 1/6834* | (2018.01) | |
| *C12Q 1/6813* | (2018.01) | |

(52) U.S. Cl.
CPC ............ *C12Q 1/6818* (2013.01); *C12Q 1/68* (2013.01); *C12Q 1/6813* (2013.01); *C12Q 1/6816* (2013.01); *C12Q 1/6823* (2013.01); *C12Q 1/6834* (2013.01); *C12Q 1/6853* (2013.01); *C12Q 1/6876* (2013.01)

(58) Field of Classification Search
None
See application file for complete search history.

(56) References Cited

U.S. PATENT DOCUMENTS

| | | |
|---|---|---|
| 4,284,412 A | 8/1981 | Hansen et al. |
| 4,498,766 A | 2/1985 | Unterleitner |
| 4,661,913 A | 4/1987 | Wu et al. |
| 4,714,682 A | 12/1987 | Schwartz |
| 4,767,206 A | 8/1988 | Schwartz |
| 4,774,189 A | 9/1988 | Schwartz |
| 4,851,331 A | 7/1989 | Vary et al. |
| 4,857,451 A | 8/1989 | Schwartz |
| 4,942,124 A | 7/1990 | Church |
| 4,989,977 A | 2/1991 | North |
| 5,137,806 A | 8/1992 | LeMaistre et al. |
| 5,160,974 A | 11/1992 | Siegel et al. |
| 5,478,722 A | 12/1995 | Caldwell |
| 5,525,494 A | 6/1996 | Newton |
| 5,573,906 A | 11/1996 | Bannwarth et al. |
| 5,595,890 A | 1/1997 | Newton et al. |
| 5,639,611 A | 1/1997 | Wallace et al. |
| 5,654,413 A | 8/1997 | Brenner |
| 5,866,336 A | 2/1999 | Nazarenko et al. |
| 5,874,260 A | 2/1999 | Cleuziat et al. |
| 5,981,180 A | 11/1999 | Chandler et al. |
| 6,103,463 A | 8/2000 | Chetverin et al. |
| 6,287,778 B1 | 9/2001 | Huang et al. |
| 6,322,971 B1 | 11/2001 | Chetverin et al. |
| 6,803,201 B2 | 10/2004 | Sorge et al. |
| 6,964,847 B1 * | 11/2005 | Englert .................. C07H 21/04 382/129 |
| 7,226,737 B2 | 6/2007 | Pancoska et al. |
| 7,955,802 B2 | 6/2011 | Whitman et al. |
| 8,288,105 B2 | 10/2012 | Whitman et al. |
| 8,846,317 B2 | 9/2014 | Whitman et al. |
| 2002/0006617 A1 * | 1/2002 | Fan ....................... C12Q 1/6858 435/6.11 |
| 2003/0087240 A1 | 5/2003 | Whitcombe et al. |

(Continued)

FOREIGN PATENT DOCUMENTS

| | | |
|---|---|---|
| CN | 1836050 A | 9/2006 |
| EP | 0658621 | 6/1995 |

(Continued)

OTHER PUBLICATIONS

Bohnert et al., "Use of Specific Oligonucleotides for Direct Enumeration of Listeria monocytogenes in Food Samples by Colony Hybridization and Rapid Detection," *Res. Microbial.*, 143:271-280, 1992.

(Continued)

*Primary Examiner* — Suryaprabha Chunduru
(74) *Attorney, Agent, or Firm* — Parker Highlander PLLC

(57) ABSTRACT

Methods and compositions for nucleic acid amplification, detection, and genotyping techniques are disclosed. In one embodiment, a nucleic acid molecule having a target-specific primer sequence; an anti-tag sequence 5' of the target-specific primer sequence; a tag sequence 5' of the anti-tag sequence; and a blocker between the anti-tag sequence and the tag sequence is disclosed. Compositions containing such a nucleic acid molecule and methods of using such a nucleic acid molecule are also disclosed.

13 Claims, 23 Drawing Sheets

Specification includes a Sequence Listing.

(56) References Cited

U.S. PATENT DOCUMENTS

| | | | |
|---|---|---|---|
| 2003/0113781 A1* | 6/2003 | Bortolin | C12Q 1/6818 435/6.11 |
| 2004/0203035 A1 | 10/2004 | Mast et al. | |
| 2005/0106564 A1 | 5/2005 | Hechinger | |
| 2005/0191625 A1 | 9/2005 | Kobler et al. | |
| 2007/0082862 A1 | 4/2007 | Takaku et al. | |
| 2007/0092880 A1 | 4/2007 | Crothers et al. | |
| 2007/0160992 A1 | 7/2007 | Bortolin et al. | |
| 2007/0172841 A1 | 7/2007 | Wang | |
| 2008/0138803 A1 | 6/2008 | Galvan-Goldman et al. | |
| 2008/0199916 A1 | 8/2008 | Zheng et al. | |
| 2008/0305481 A1 | 12/2008 | Whitman et al. | |
| 2009/0136956 A1 | 5/2009 | Merante et al. | |
| 2009/0141951 A1 | 6/2009 | Ogo et al. | |
| 2009/0142752 A1 | 6/2009 | Hall et al. | |
| 2009/0148849 A1 | 6/2009 | Galvan-Goldman et al. | |
| 2010/0203572 A1 | 8/2010 | Lehmann et al. | |
| 2011/0223602 A1 | 9/2011 | Whitman et al. | |
| 2013/0116141 A1 | 5/2013 | Whitman et al. | |

FOREIGN PATENT DOCUMENTS

| | | |
|---|---|---|
| EP | 1 088 102 B1 | 7/2003 |
| JP | 2001/513623 | 9/2001 |
| JP | 2004-205414 | 7/2004 |
| JP | 2008-048648 | 3/2008 |
| WO | WO 1993/17126 | 9/1993 |
| WO | WO 1997/31256 | 8/1997 |
| WO | WO 1998/002449 | 1/1998 |
| WO | WO 1999/066071 | 12/1999 |
| WO | WO 2001/094625 | 12/2001 |
| WO | WO 2003/035864 | 5/2003 |
| WO | WO 2005/007815 | 1/2005 |
| WO | WO 2005/100594 | 10/2005 |
| WO | WO 2006/002525 | 1/2006 |
| WO | WO 2006/002526 | 1/2006 |
| WO | WO 2005/047533 | 5/2006 |
| WO | WO 2006/071770 | 7/2006 |
| WO | WO 2008/074023 | 6/2008 |
| WO | WO 2009/008854 | 1/2009 |
| WO | WO 2009/074882 | 6/2009 |

OTHER PUBLICATIONS

Corless et al., "Simultaneous Detection of *Neisseria meningitidis, Haemophilus influenzae*, and *Streptococcus pneumoniae* in Suspected Cases of Mengitis and Septicemia Using Real-Time PCR," *Journal of Microbiology*, 39:1553-1558, 2001.

Egholm et al., "PNA hybridizes to complementary oligonucleotides obeying the Watson-Crick hydrogen bonding rules," *Nature*, 365: 566-568, 1993.

Extended European Search Report issued in European Patent Application No. 10800291.6 dated Sep. 10, 2012.

Fodor et al., "A Pancreatic Exocrine Cell Factor and AP4 Bind Overlapping Sites in the Amylase 2A Enhancer," *Biochemistry*, 8102-8108, 1991.

Froehler et al., "Synthesis of DNA via deoxynucleoside H-phosphonate intermediates," *Nucleic Acids Research*, 14(13):5399-5407, 1986.

Fujimara et al., "Rapid multiplex single nucleotide polymorphism genotyping based on single base extension reactions and color-coded beads," *Journal of Bioscience and Bioengineering*, 94(4): 368-370, 2002.

Holmstream et al., "A Highly sensitive and Fast Nonradioactive Method for Detection of Polymerase Chain Reaction Products," *Analytical Biochemistry*, 209:278-283, 1993.

Huber et al., "Accessing single nucleotide polymorphisms in genomic DNA by direct multiplex polymerase chain reaction amplification on oligonucleotide microarrays," *Analytical Biochemistry*, 303:25-33, 2002.

Johnson et al., "Detection of Genes Coding for Listerilysin and Listeria moncytogenes Antigen A (LmaA) in *Listeria* spp. by the Polymerase Chain Reaction," *Microbial Pathogenesis*, 12:79-86, 1992.

Koo et al., "Multiplexed genotyping of ABC transporter polymorphisms with the Bioplex suspension tray," *Biol. Proced Online.*, 9(1):27-42, 2006.

Koshkin and Wengel, Synthesis of Novel 2',3'—Linked Bicyclic Thymine Ribonucleosides, *J. Org. Chem.*, 63:2778-2781, 1998.

Kwoh et al., "Transcription—based amplification system and detection of amplified human immunodeficiency virus type 1 with a bead-based sandwich hybridization format," *Proc. Natl. Acad. Sci. USA*, 86:1173-1177, 1989.

Lars et al., "Primer-design for multiplexed genotyping," *Nucleic Acids Research*, 31(6): 1796-1802, 2003.

Letant et al., "Multiplexed reverse transcriptase PCR assay for identification of viral respiratory pathogens at the Point of Care," *Journal of Clinical Microbiology*, 45(11):3498-3505, 2007.

Maaroufi et al., "Real-Time PCR for Determining Capsular Serotypes of *Haemophilus influenzae*, " *Journal of Clinical Microbiolgy*, 45:2305-2308, 2007.

Mahony et al., "Development of a respiratory virus panel test for detection of twenty human respiratory viruses by use of multiplex PCR and a fluid microbead-based assay," *Journal of Clinical Microbiology*, 45(9):2965-2970, 2007.

Maldonado-Rodriguez et al., "Mutation detection by stacking hybridization or genosensor arrays," *Molecular Biotechnology*, 11(1):13-25, 1999.

Office Action (along with English translation) issued in Japanese Divisional Patent Application No. 2015-147338, dated Jul. 13, 2016.

Official Action issued in Japanese Application No. 2015-147338 dated May 10, 2017.

Official Action issued in Japanese Application No. 2015-147338 dated Nov. 27, 2017.

Office Action issued in corresponding Japanese Application No. 2017-248991, dated Jan. 16, 2019.

Office Communication issued in U.S. Appl. No. 12/826,189 dated Sep. 7, 2012.

Office Communication issued in U.S. Appl. No. 12/826,189 dated Jan. 28, 2013.

Office Communication issued in U.S. Appl. No. 12/826,189 dated Jun. 11, 2013.

Office Communication issued in U.S. Appl. No. 12/826,189 dated Aug. 19, 2013.

Office Communication issued in U.S. Appl. No. 12/826,189 dated Jan. 21, 2014.

Office Communication issued in U.S. Appl. No. 14/270,785, dated Feb. 1, 2016.

Office Communication issued in U.S. Appl. No. 14/270,785, dated Jul. 20, 2016.

Office Communication issued in U.S. Appl. No. 14/270,785, dated Dec. 22, 2016.

PCT International Search Report and Written Opinion, issued in International application No. PCT/US2010/040354, dated Mar. 15, 2011.

Peyret et al., "Nearest-Neighbor Thermodynamics and NMR of DNA Sequences with Internal A.A, C.C, G.G, and T.T Mismatches," *Biochemistry*, 38:3468-3477, 1999.

Ramussen et al., "Covalent Immobilization of DNA onto Polystyrene Microwells: The Molecules are only bound at the 5' End," *Analytical Biochemistry*, 198:138-142, 1991.

Response to Office Communication issued in U.S. Appl. No. 12/826,189 dated Nov. 28, 2012.

Response to Office Communication issued in U.S. Appl. No. 12/826,189 dated Apr. 26, 2013.

Response to Office Communication issued in U.S. Appl. No. 12/826,189 dated Nov. 19, 2013.

Rödiger, et al., "A highly versatile microscope imaging technology platform for the multiplex real-time detection of biomolecules and autoimmune antibodies," *Adv. Biochem. Eng. Biotechnol.*, 133:35-74, 2013.

Untranslated Chinese Office Action (along with foreign associate's English summary) issued in Chinese Patent Application No. 201080035685.3, dated Apr. 14, 2014.

(56) References Cited

OTHER PUBLICATIONS

Wahlestedt et al., "Potent and nontoxic antisense oligonucleotides containing locked nucleic acids," *Proc. Natl. Acad. Sci. US A*, 97:5633-5638, 2000.
Walker et al., "Strand displacement amplification—an isothermal, in vitro DNA amplification technique," *Nucleic Acids Research*, 20(7): 1691-1696, 1992.

* cited by examiner

Labels are fluorophores involved in a FRET pair, either donor or acceptor

Labels are fluorophores involved in a FRET pair, either donor or acceptor

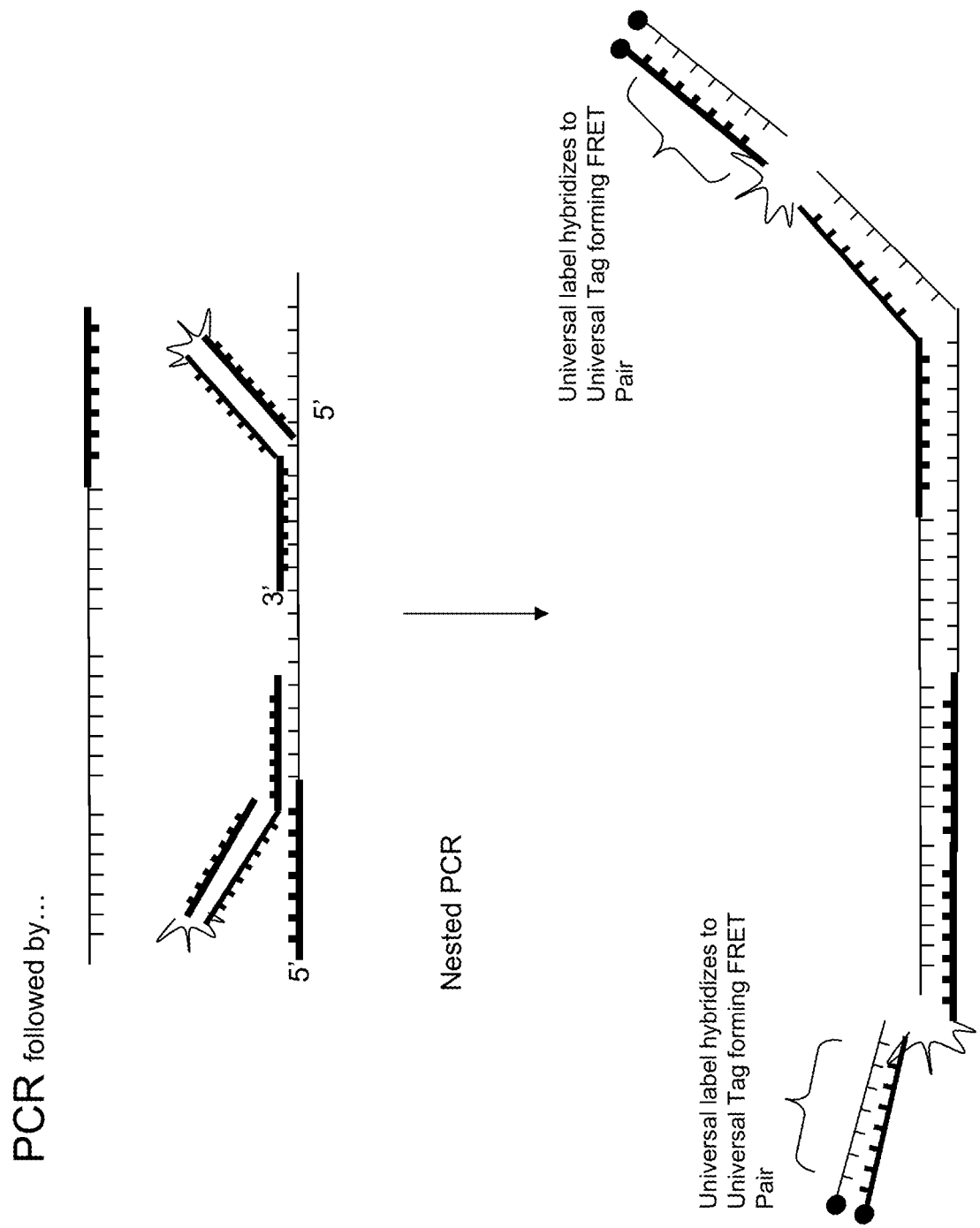

CHIMERIC PRIMERS WITH HAIRPIN CONFORMATIONS AND METHODS OF USING SAME

This application is a continuation of U.S. patent application Ser. No. 14/270,785, filed on May 6, 2014, which is a divisional of U.S. patent application Ser. No. 12/826,189, filed on Jun. 29, 2010, now U.S. Pat. No. 9,587,270, which claims priority to U.S. Provisional Application Ser. No. 61/221,271, filed on Jun. 29, 2009, the entirety of which is incorporated by reference.

BACKGROUND OF THE INVENTION

1. Field of the Invention

The present invention relates generally to the fields of genetics and molecular biology. More particularly, it concerns methods and compositions for the amplification and detection of nucleic acids.

2. Description of Related Art

Nucleic acid amplification and detection techniques are frequently employed in analyzing DNA samples for mutations and polymorphisms. They are also employed in the detection and typing of bacteria, virus, and fungi, including those that are infectious pathogens, by analysis of their DNA or RNA. Approaches such as allele-specific PCR (AS-PCR) and allele-specific primer extension (ASPE) detect mutations and polymorphisms using oligonucleotide primers selected such that they selectively achieve primer extension of either a sequence containing a variant nucleotide or the corresponding sequence containing the wild-type nucleotide. Such approaches are described in, for example, U.S. Pat. Nos. 5,595,890, 5,639,611, and 5,137,806, the disclosures of which are incorporated by reference.

U.S. application Ser. No. 12/262,842, which is incorporated by reference, describes methods and compositions that can simplify genetic analysis by methods such as the allele-specific primer extension (ASPE) and allele-specific PCR (AS-PCR) methods mentioned above. In certain embodiments, the '842 application employs a primer with a tag sequence 5' of the target specific sequence, and a capture complex comprising an anti-tag sequence complementary to the primer's tag sequence in a method for a "one-step" assay. The '842 application discloses that its one-step amplification and detection methods can reduce the multiple assay steps in the current commercially available Luminex Tag-It® technology platform to a single-step.

Despite the usefulness of the above-mentioned techniques, better methods of nucleic acid amplification and detection that can provide assays that require less optimization of primer concentrations; provide quicker results; have lower non-specific background and higher specific signal when using DNA binding dyes; provide more sensitive detection in general; provide a more perfect representation of product/target concentration; and allow higher multiplexing of primer sets are needed. The methods and composition of the present invention meet these needs as described below.

SUMMARY OF THE INVENTION

The methods and compositions of the present invention provide nucleic acid amplification, detection, and genotyping techniques. In one embodiment, the present invention provides a nucleic acid molecule comprising: a target-specific primer sequence; an anti-tag sequence 5' of the target-specific primer sequence; a tag sequence 5' of the anti-tag sequence; and a blocker between the anti-tag sequence and the tag sequence.

In another embodiment, the present invention provides a composition comprising: a microsphere; a first anti-tag nucleic acid covalently attached to the microsphere; a tag nucleic acid hybridized to the first anti-tag nucleic acid; a blocker covalently attached 3' of the tag sequence; a second anti-tag nucleic acid, which has an identical sequence to the first anti-tag nucleic acid, covalently attached 3' of the blocker; a target-specific nucleic acid covalently attached 3' of the second anti-tag nucleic acid; and a nucleic acid molecule hybridized to the second anti-tag nucleic acid and the target-specific nucleic acid, wherein the nucleic acid molecule comprises a sequence that is complementary to the sequence of the anti-tag nucleic acid and the target-specific nucleic acid.

In another embodiment, the present invention provides a composition comprising: (a) a first nucleic acid molecule, wherein the first nucleic acid molecule is a first member of a primer pair, comprising: (i) a first target-specific primer sequence; (ii) an anti-tag sequence 5' of the target-specific primer sequence; (iii) a tag sequence 5' of the anti-tag sequence; and (iv) a blocker between the anti-tag sequence and the tag sequence; and (b) a second nucleic acid molecule, wherein the second nucleic acid molecule is a second member of a primer pair, comprising: (i) a second target-specific primer sequence; (ii) a universal anti-tag sequence 5' of the target-specific primer sequence; (iii) a universal tag sequence 5' of the anti-tag sequence; and (iv) a blocker between the anti-tag sequence and the tag sequence; and (c) a third nucleic acid molecule comprising: (i) a universal anti-tag sequence complementary to the universal tag sequence; and (ii) a label.

In other embodiments, the present invention provides a composition comprising a plurality of primer pairs for the amplification of a plurality of different target sequences, each primer pair comprising: (a) a first nucleic acid molecule comprising: (i) a first target-specific primer sequence; (ii) an anti-tag sequence 5' of the target-specific primer sequence; (iii) a tag sequence 5' of the anti-tag sequence; and (iv) a blocker between the anti-tag sequence and the tag sequence; and (b) a second nucleic acid molecule comprising: (i) a second target-specific primer sequence; (ii) a universal anti-tag sequence 5' of the target-specific primer sequence; (iii) a universal tag sequence 5' of the anti-tag sequence; and (iv) a blocker between the anti-tag sequence and the tag sequence; and (c) a labeled, universal anti-tag molecule comprising: (i) a universal anti-tag sequence complementary to the universal tag sequence; and (ii) a label.

A composition comprising: (a) a first nucleic acid molecule, wherein the first nucleic acid molecule is a first member of a primer pair, comprising: (i) a first target-specific primer sequence; (ii) a universal anti-tag sequence 5' of the target-specific primer sequence; (iii) a universal tag sequence 5' of the anti-tag sequence; and (iv) a blocker between the anti-tag sequence and the tag sequence; (b) a second nucleic acid molecule, wherein the second nucleic acid molecule is a second member of a primer pair, comprising: (i) a second target-specific primer sequence; (ii) a universal anti-tag sequence 5' of the target-specific primer sequence; (iii) a universal tag sequence 5' of the anti-tag sequence; and (iv) a blocker between the anti-tag sequence and the tag sequence; and (c) a third nucleic acid molecule comprising: (i) a universal anti-tag sequence complementary to the universal tag sequences on the first and second nucleic acid molecules; and (ii) a label.

In one embodiment, the invention provides a nucleic acid molecule comprising from 5' to 3', a tag region of 24 nucleotide bases, an internal C18 blocker, a variable length sequence that is complimentary to a portion of the tag region, and a target-specific primer region, which may be of variable length. The length and composition of the sequence complimentary to a portion of the tag region can be optimized according to buffer composition, hybridization conditions, and the sequence of the tag region. Optimally, the binding of the tag region to the complimentary sequence should form a hairpin structure with sufficient thermodynamic stability so as to remain in a closed hairpin formation prior to second strand synthesis during amplification, but the energy barrier should be sufficiently low to allow disruption of the hairpin structure during second strand synthesis.

The tag and anti-tag regions in a hairpin-forming nucleic acid molecule as described herein may be identical in length or they may be of different lengths. For example, the tag and anti-tag regions could both be 24 nucleotides long, or one region could be 24 nucleotides long while the other region is shorter (e.g., 8-16 nucleotides). It can be advantageous to use tag and anti-tag regions of different lengths in order to alter the hybridization properties of the hairpin-forming nucleic acid molecule. Preferably, the hairpin region of the molecule is designed such that it has a strong enough binding energy to remain in the closed state until the formation of a double-stranded amplicon product causes the hairpin region to open, but a weak enough binding energy so as to remain in the open state in the presence of the double stranded product. Another consideration is the strength of the binding between the tag region of a primer and the anti-tag region used to capture and/or label (e.g., an anti-tag sequence immobilized on a bead) an amplicon synthesized from the primer. A person of skill in the art will be familiar with factors affecting DNA hybridization, such as sequence length and G+C content, and will be able to determine the appropriate lengths for the tag and anti-tag regions in a hairpin-forming nucleic acid molecule in order to achieve the properties mentioned above for a particular application.

In one embodiment, a nucleic acid molecule is provided that comprises, from 5' to 3', a tag region of 24 nucleotide bases followed by an internal C18 blocker, which is then followed by 12 bases that are not complimentary to other nucleic acids in the reaction, followed by 12 bases that are complimentary to the first 12 bases of the tag region, followed by a target-specific primer region, which may be of variable length.

In one embodiment, a nucleic acid molecule is provided that comprises, from 5' to 3', a tag region of 24 nucleotide bases followed by an internal C18 blocker, which is then followed by 12 bases that are complimentary to the first 12 bases of the tag region, followed by a target-specific primer region, which may be of variable length.

A target nucleic acid may be any nucleic acid of interest, and the sample containing the target nucleic acid may be any sample that contains or is suspected of containing nucleic acids. In certain aspects of the invention the sample is, for example, from a subject who is being screened for the presence or absence of one or more genetic mutations or polymorphisms. In another aspect of the invention the sample may be from a subject who is being tested for the presence or absence of a pathogen. Where the sample is obtained from a subject, it may be obtained by methods known to those in the art, such as aspiration, biopsy, swabbing, venipuncture, spinal tap, fecal sample, or urine sample. In certain embodiments the subject is a mammal, bird, or fish. The mammal may be, for example, a human, cat, dog, cow, horse, sheep, swine, swine, rabbit, rat, or mouse. In some aspects of the invention, the sample is an environmental sample such as a water, soil, or air sample. In other aspects of the invention, the sample is from a plant, bacteria, virus, fungi, protozoan, or metazoan.

A primer is a nucleic acid that is capable of priming the synthesis of a nascent nucleic acid in a template-dependent process. A target-specific primer refers to a primer that has been designed to prime the synthesis of a particular target nucleic acid. A primer pair refers to two primers, commonly known as a forward primer and a reverse primer or as an upstream primer and a downstream primer, which are designed to amplify a target sequence between the binding sites of the two primers on a template nucleic acid molecule. In certain embodiments, the primer has a target-specific sequence that is between 10-40, 15-30, or 18-26 nucleotides in length.

Various aspects of the present invention use sets of complementary tag and anti-tag sequences. The tags and anti-tags are preferably non-cross hybridizing, i.e., each tag and anti-tag should hybridize only to its complementary partner, and not to other tags or anti-tags in the same reaction. Preferably, the tags and anti-tags also will not hybridize to other nucleic acids in the sample during a reaction. The proper selection of non-cross hybridizing tag and anti-tag sequences is useful in assays, particularly assays in a highly parallel hybridization environment, that require stringent non-cross hybridizing behavior. In certain embodiments, the tag and anti-tag sequences are between 6 to 60, 8 to 50, 10 to 40, 10 to 20, 12 to 24, or 20 to 30 nucleotides in length. In some embodiments, the tag and anti-tag sequences are 12, 14, 16, or 24 nucleotides in length. A number of tag and tag complement (i.e., anti-tag) sequences are known in the art and may be used in the present invention. For example, U.S. Pat. No. 7,226,737, incorporated herein by reference, describes a set of 210 non-cross hybridizing tags and anti-tags. In addition, U.S. Published Application No. 2005/0191625, incorporated herein by reference, discloses a family of 1168 tag sequences with a demonstrated ability to correctly hybridize to their complementary sequences with minimal cross hybridization. A "universal" tag or anti-tag refers to a tag or anti-tag that has the same sequence across all reactions in a multiplex reaction.

A blocker is a moiety that inhibits extension of the nascent nucleic acid sequence during second strand synthesis. Non-limiting examples of blocker moieties include C6-20 straight chain alkylenes, iSp18 (which is an 18-atom hexa-ethyleneglycol), iMe-isodC, a hexethylene glycol monomer, synthetic nucleic acid bases, 2-O-alkyl RNA, or an oligonucleotide sequence in the reverse orientation as compared to the target specific sequence.

In certain aspects of the invention, a solid support is used. A variety of solid supports for the immobilization of biomolecules are known. For example, the solid support may be nitrocellulose, nylon membrane, glass, activated quartz, activated glass, polyvinylidene difluoride (PVDF) membrane, polystyrene substrates, polyacrylamide-based substrate, other polymers, copolymers, or crosslinked polymers such as poly(vinyl chloride), poly(methyl methacrylate), poly(dimethyl siloxane), photopolymers (which contain photoreactive species such as nitrenes, carbenes and ketyl radicals capable of forming covalent links with target molecules). A solid support may be in the form of, for example, a bead (microsphere), a column, or a chip. Molecules immobilized on planar solid supports are typically identified by their spatial position on the support. Molecules immobilized on non-planar solid supports, such as beads, are often identified by some form of encoding of the support, as discussed below.

Beads may be encoded such that one subpopulation of beads can be distinguished from another subpopulation. Encoding may be by a variety of techniques. For example, the beads may be fluorescently labeled with fluorescent dyes having different emission spectra and/or different signal intensities. In certain embodiments, the beads are Luminex FlexMAP™ microspheres or Luminex xMAP® microspheres. The size of the beads in a subpopulation may also be used to distinguish one subpopulation from another. Another method of modifying a bead is to incorporate a magnetically responsive substance, such as $Fe_3O_4$, into the structure. Paramagnetic and superparamagnetic microspheres have negligible magnetism in the absence of a magnetic field, but application of a magnetic field induces alignment of the magnetic domains in the microspheres, resulting in attraction of the microspheres to the field source. Combining fluorescent dyes, bead size, and/or magnetically responsive substances into the beads can further increase the number of different subpopulations of beads that can be created.

In certain aspects of the invention, the composition comprises a plurality of anti-tag nucleic acid molecules covalently attached to a plurality of encoded microspheres, wherein the plurality of anti-tag molecules comprise anti-tag sequences that are complementary to the tag sequences in the plurality of primer pairs, and wherein the identity of each of the anti-tag nucleic acid molecules can be determined from the encoding of the encoded microsphere to which it is covalently attached.

Nucleic acids in the methods and compositions described herein may be labeled with a reporter. A reporter is a molecule that facilitates the detection of a molecule to which it is attached. Numerous reporter molecules that may be used to label nucleic acids are known. Direct reporter molecules include fluorophores, chromophores, and radiophores. Non-limiting examples of fluorophores include, a red fluorescent squarine dye such as 2,4-Bis[1,3,3-trimethyl-2-indolinylidenemethyl] cyclobutenediylium-1,3-dioxolate, an infrared dye such as 2,4 Bis [3,3-dimethyl-2-(1H-benz[e] indolinylidenemethyl)] cyclobutenediylium-1,3-dioxolate, or an orange fluorescent squarine dye such as 2,4-Bis [3,5-dimethyl-2-pyrrolyl] cyclobutenediylium-1,3-diololate. Additional non-limiting examples of fluorophores include quantum dots, Alexa Fluor® dyes, AMCA, BODIPY® 630/650, BODIPY® 650/665, BODIPY®-FL, BODIPY®-R6G, BODIPY®-TMR, BODIPY®-TRX, Cascade Blue®, CyDye™, including but not limited to Cy2™, Cy3™, and Cy5™, a DNA intercalating dye, 6-FAM™, Fluorescein, HEX™, 6-JOE, Oregon Green® 488, Oregon Green® 500, Oregon Green® 514, Pacific Blue™, REG, phycobilliproteins including, but not limited to, phycoerythrin and allophycocyanin, Rhodamine Green™, Rhodamine Red™, ROX™ TAMRA™, TET™, Tetramethylrhodamine, or Texas Red®. A signal amplification reagent, such as tyramide (PerkinElmer), may be used to enhance the fluorescence signal. Indirect reporter molecules include biotin, which must be bound to another molecule such as streptavidin-phycoerythrin for detection. In a multiplex reaction, the reporter attached to the primer or the dNTP may be the same for all reactions in the multiplex reaction if the identities of the amplification products can be determined based on the specific location or identity of the solid support to which they hybridize.

In other embodiments, methods for amplifying a target nucleic acid are provided, which comprise: (a) providing a first primer pair comprising: (i) a first primer comprising: a first target-specific primer sequence; an anti-tag sequence 5' of the target-specific primer sequence; a tag sequence 5' of the anti-tag sequence; and a blocker between the anti-tag sequence and the tag sequence; and (ii) a second primer comprising: a second target-specific primer sequence; (b) providing a reporter; (c) providing a capture complex comprising an anti-tag sequence attached to a solid support; (d) amplifying the target nucleic acid by combining the first primer pair, the reporter, the capture complex, and a sample comprising the target nucleic acid under conditions suitable for amplification of the target nucleic acid. In certain aspects, the reporter is attached to the second primer. In other aspects, the reporter is attached to a dNTP. In yet other embodiments, the reporter is a DNA intercalator. In some embodiments, the method further comprises hybridizing the amplified target nucleic acid to the anti-tag sequence of the capture complex. In still further embodiments, the method further comprises detecting the hybridized, amplified target nucleic acid. Detecting the amplified nucleic acid may comprise, for example, imaging the amplified target nucleic acid sequence bound to the capture complex. In some embodiments, the sample comprises at least a second target nucleic acid, and at least a second primer pair is combined with the first primer pair, the reporter, the capture complex, and the sample comprising the target nucleic acids under conditions suitable for amplification of the target nucleic acids. The different amplified target nucleic acids may be hybridized to different anti-tag sequences of distinguishable capture complexes. The capture complexes may be, for example, spatially distinguishable and/or optically distinguishable.

The hairpin forming primers disclosed herein can also be used to amplify and detect target nucleic acid sequences without the use of a capture complex. For example, in one embodiment a target nucleic acid can be amplified by a method comprising: (a) providing a first primer pair comprising: (i) a first target-specific primer sequence; an anti-tag sequence 5' of the target-specific primer sequence; a tag sequence 5' of the anti-tag sequence; a blocker between the anti-tag sequence and the tag sequence; and a chromophore attached to the tag sequence; and (ii) a second primer comprising: a second target-specific primer sequence; an anti-tag sequence 5' of the target-specific primer sequence; a tag sequence 5' of the anti-tag sequence; a blocker between the anti-tag sequence and the tag sequence; and a chromophore attached to the tag sequence; and (b) a label nucleic acid molecule comprising: (i) an anti-tag sequence complementary to the universal tag sequences of the first primer pair; and (ii) a chromophore capable of Forster Resonance Energy Transfer with the chromophores of the first primer pair; and (d) amplifying the target nucleic by combining the first primer pair, the universal label nucleic acid molecule, and a sample comprising the target nucleic acid under conditions suitable for amplification of the target nucleic acid. The method may further comprise detecting the amplified nucleic acid. The detection may comprise detecting the FRET between the chromophores of the first primer pair and the chromophore of the universal label. In certain embodiments, the detection is performed in real-time (i.e., the method provides a real-time PCR). This amplification method can be multiplexed, wherein the sample comprises at least a second target nucleic acid and a second primer pair. For multiplexed applications, each primer pair and corresponding label nucleic acid molecule need to have different tag and anti-tag sequences from any other primer pairs and label nucleic acid molecules in the reaction. Additionally, the labels with different emission wavelengths need to be used for each different primer pair in the reaction. In some embodiments the primer pair is a nested primer pair and the target nucleic acid is itself an amplicon.

The hairpin forming probes disclosed herein may also be used to detect the products of cleavage reactions. Several cleavage-based assays for the detection of nucleic acid sequences are know in the art. For example, Invader technology, which uses a structure-specific flap endonuclease (FEN) to cleave a three-dimensional complex formed by hybridization of allele-specific overlapping oligonucleotides to target DNA containing a single nucleotide polymorphism (SNP) (single nucleotide polymorphism) site, is well-known for use in SNP discrimination. Mung bean nuclease and 51 nuclease are also known for their use in SNP discrimination because of their ability to cleave single base mismatches. In one embodiment, the present invention provides a method for detecting a cleavage product of a nucleic acid cleavage reaction comprising: (a) providing an oligonucleotide probe comprising: (i) a cleavage-product specific sequence; (ii) an anti-tag sequence 5' of the cleavage-product specific sequence; (iii) a tag sequence 5' of the anti-tag sequence; (iv) a blocker between the anti-tag sequence and the tag sequence; and (v) a label; (b) hybridizing the oligonucleotide probe to the cleavage product; (c) extending the cleavage product so as to displace the tag sequence from its hybridization to the anti-tag sequence; (d) hybridizing a labeled anti-tag probe to the displaced tag sequence and (e) detecting the hybridization and extension of the oligonucleotide probe to the cleavage product. The label may be, for example, a FRET donor or acceptor molecule. This method may be performed with or without immobilizing the oligonucleotide probe on a solid support. In embodiments where the probe is immobilized, the immobilization may be achieved by hybridization of the tag sequence of the probe to a complementary anti-tag sequence coupled to a solid support (e.g., a bead or planar array). As discussed above, cleavage products may be created by a variety of technologies including, without limitation, those that employ a structure-specific flap endonuclease, a mung bean nuclease, or an Si nuclease. Those of skill in the art will be able to design probes that are susceptible to cleavage when hybridized to particular target sequence.

Additionally, the hairpin forming probes disclosed herein may be used to detect the formation of a ligation product. A ligation product can be formed when two oligonucleotide probes bind adjacent to one another on a target nucleic acid. Typically, the ligation is achieved using a ligase enzyme. In one embodiment, the present invention provides a method for detecting a ligation product comprising: (a) providing an oligonucleotide probe comprising: (i) a ligation-product specific sequence; (ii) an anti-tag sequence 5' of the ligation-product specific sequence; (iii) a tag sequence 5' of the anti-tag sequence; (iv) a blocker between the anti-tag sequence and the tag sequence; and (v) a label; (b) hybridizing the oligonucleotide probe to the ligation product at a temperature at which the ligation product hybridizes to the olignucleotide probe but at which unligated subunits of the ligation product do not hybridize to the oligonucleotide probe; (c) extending the ligation product so as to displace the tag sequence from its hybridization to the anti-tag sequence; (d) hybridizing a labeled anti-tag probe to the displaced tag sequence and (e) detecting the hybridization and extension of the oligonucleotide probe to the ligation product. The label may be, for example, a FRET donor or acceptor molecule. This method may be performed with or without immobilizing the oligonucleotide probe on a solid support. In embodiments where the probe is immobilized, the immobilization may be achieved by hybridization of the tag sequence of the probe to a complementary anti-tag sequence coupled to a solid support (e.g., a bead or planar array). Those of skill in the art will be able to design probes that can be ligated together to create a ligation product when hybridized to particular target sequence.

In one embodiment, the present invention provides a method for quantifying gene expression comprising: reverse transcribing mRNA from a target gene to form cDNA; hybridizing to the cDNA a first oligonucleotide comprising a universal primer-binding sequence and a cDNA-specific sequence, and a second oligonucleotide comprising a unique primer-binding sequence and a cDNA-specific sequence; ligating the first oligonucleotide to the second oligonucleotide to form a ligated oligonucleotide; amplifying the ligated oligonucleotide using a universal primer and a unique primer, the unique primer comprising a unique primer sequence, an anti-tag sequence 5' of the unique primer sequence, a tag sequence 5' of the anti-tag sequence, and a blocker between the anti-tag sequence and the tag sequence; capturing the amplicon by hybridizing the tag sequence of the amplicon to an anti-tag sequence of a capture complex; labeling the captured amplicon; and detecting and quantifying the labeled, captured amplicon. The cDNA can optionally be immobilized if a wash steps is performed after the reverse transcription reaction. Methods for ligation-mediated amplification are known in the art and described in, for example, Peck et al., Genome Biology, 7:R61 (2006), which is incorporated herein by reference. In the context of a multiplexed reaction in which the expression of multiple target genes is analyzed, the "universal primer" and "universal primer-binding sequence" refer to a common primer and a sequence complementary thereto used to analyze all targets in the reaction. In certain embodiments, the universal primer is a T3 primer. In contrast, the "unique primer" and "unique primer-binding sequence" refer to a primer and a sequence complementary thereto that is specific for each different target gene being analyzed. The "unique primer" and "unique primer-binding sequence," however, are not complementary to a sequence in the target gene itself. The "unique primer" and "unique primer-binding sequence" may be a tag/anti-tag set, but should not be complementary to any other tag or anti-tag sequence in a multiplexed reaction. In multiplexed reactions, for each of the plurality of different targets being assayed, there is a unique combination of tag sequence, anti-tag sequence, and capture complex, which will permit the amplicons for each target to be distinguished from that of every other target.

The cDNA may be immobilized by methods known to those in the art. In particular embodiments, the cDNA is immobilized by capturing and reverse transcribing the mRNA on an oligo-dT coated well or bead.

In other embodiments, the present invention provides a method of detecting microorganisms in a sample comprising: (a) providing a plurality of primer pairs for the amplification of a plurality of different target nucleic acid sequences from a plurality of different microorganisms, each primer pair comprising: (i) a first primer comprising: a first target-specific primer sequence; an anti-tag sequence 5' of the target-specific primer sequence; a tag sequence 5' of the anti-tag sequence; and a blocker between the anti-tag sequence and the tag sequence; and (ii) a second primer comprising: a second target-specific primer sequence; a universal anti-tag sequence 5' of the target-specific primer sequence; a universal tag sequence 5' of the anti-tag sequence; and a blocker between the anti-tag sequence and the tag sequence; (b) providing labeled, universal anti-tag molecules comprising: (i) a universal anti-tag sequence complementary to the universal tag sequence; and (ii) a label; (c) providing a plurality of capture complexes comprising anti-tag sequences attached to a solid support; (d) amplifying the target nucleic acid sequences from the different microorganisms, if the microorganisms are present in the sample, by combining the plurality of primer pairs, the labeled, universal anti-tag molecule, the capture complexes, and the sample under conditions suitable for amplification of the target nucleic acid sequences; (e) hybridizing the amplified target nucleic acid sequences to their respective anti-tag sequences of their respective capture complexes; and (f) detecting the microorganisms present in the sample by detecting the amplified target nucleic acid sequences bound to their respective capture complexes.

The microorganism may be, for example, a bacteria, virus, retrovirus, or fungus. In certain embodiments, the microorganism is a pathogen. The sample that contains or may contain the microorganism may be a patient sample, such as a blood sample, serum sample, cerebral spinal fluid sample, stool sample, broncoalveolar lavage sample, sputum, pericardial fluid, peritoneal fluid, pleural fluid, urine, gastric aspirate, abscess, tracheal aspirate, bronchial washing, bone marrow, tissue, etc. In other embodiments, the sample is an environmental sample, such as a water sample or a soil sample. In certain embodiments, between 2 to 100 primer pairs are provided for detecting 2 to 100 different microorganisms. Each primer pair may be designed to detect a different microorganism or there can be some redundancy in which two or more primer pairs are designed to detect the same microorganism. Typically in a clinical/diagnostic setting or in an environmental setting only a subset of the microorganisms being screened for are expected to be present in patient sample or the environmental sample. For example, while a patient sample may be screened for 30 different microorganisms, the patient sample will likely contain only about 0 to 2 of these microorganisms, as it is uncommon for someone to be infected with a large number of different microorganism at the same time. In certain aspects of the invention, between 0 to 10, 1 to 10, 1 to 5, or 1 to 3 different microorganisms are detected.

The amplification may be qualitative, semi-quantitative, or quantitative. In certain embodiments, the amplification may be monitored in real time (e.g., real-time PCR). When amplification is by the polymerase chain reaction (PCR), a polymerase possessing strand displacement activity should be used as such a polymerase will be able to open the hairpin structure formed by the hybridization of the tag and anti-tag regions of the primer. In some embodiments, the polymerase is an exo(–) polymerase.

Certain embodiments of the invention comprise the detection of the amplified target nucleic acid. Detection of the amplified target nucleic acid may be by a variety of techniques. In one aspect of the invention, the amplified target nucleic acids are detected using a flow cytometer. Flow cytometry is particularly well-suited where the solid support of the capture complex is a bead or other particle. In other aspects of the invention, detecting the amplified target nucleic acid comprises imaging the amplified target nucleic acid sequence bound to the capture complex. The imaging may be on, for example, a bead array platform or a chip array platform.

The methods of the present invention may be used in multiplexed assays. In such multiplexed assay, the sample will typically comprise at least a second target nucleic acid sequence. In certain aspects of the invention, there are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 120, 140, 160, 180, 200, 220, 240, 260, 280, 300, 400, 500, 600, 700, 800, 900, 1000, or any range derivable therein, target nucleic acid sequences in the sample. As mentioned above, a target nucleic acid sequence may be any sequence of interest. One target nucleic acid sequence may be in the same gene or a different gene as another target nucleic acid sequence, and the target nucleic acid sequences may or may not overlap. Of course, a target nucleic acid sequence need not be within a gene but may be within, for example, a non-coding region of DNA. In a multiplex assay where at least a second target nucleic acid to be amplified is present in a sample, at least a second discriminating primer or a second primer pair is combined with the first primer pair.

An advantage of the methods described herein, is that they may be performed in a "closed tube" format. In a "closed tube" assay all reagents and sample are added at the start of the reaction, thus eliminating the need for opening of the reaction vessel to add reagents after the reaction is initiated. This typically results in a faster turn around time and reduces the opportunities for contamination and human error. Such "closed tube" assays are particularly well-suited for Point-of-Care applications in which rapid results, minimum human manipulations of the assay, and a sterile environment are desirable.

It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 16 illustrates an assay in which universal hairpin primers are combined with target specific hairpin primers for use as a nested real-time PCR assay chemistry. Upon extension of the primers the hairpin portions will open up allowing binding to a labeled probe, such that FRET occurs allowing real-time detection in standard real-time thermal cyclers. The advantage of this solution is that the end-users need only design the primers, making it very design friendly. No beads are required in this embodiment.

DESCRIPTION OF ILLUSTRATIVE EMBODIMENTS

I. Nucleic Acids

A. Primers

Primers used in the methods and compositions described herein are designed to provide better nucleic acid amplification and detection than previously available. Assays that use these primers require less optimization of primer concentrations; yield results more quickly; result in lower background and higher specific signal when using DNA binding dyes; provide greater sensitivity; provide a more accurate measure of product/target concentration; and allow higher multiplexing of primer sets. The term "primer," as used herein, is meant to encompass any nucleic acid that is capable of priming the synthesis of a nascent nucleic acid in a template-dependent process. Primers may be provided in double-stranded and/or single-stranded form, although the single-stranded form is preferred.

Figure 1A:
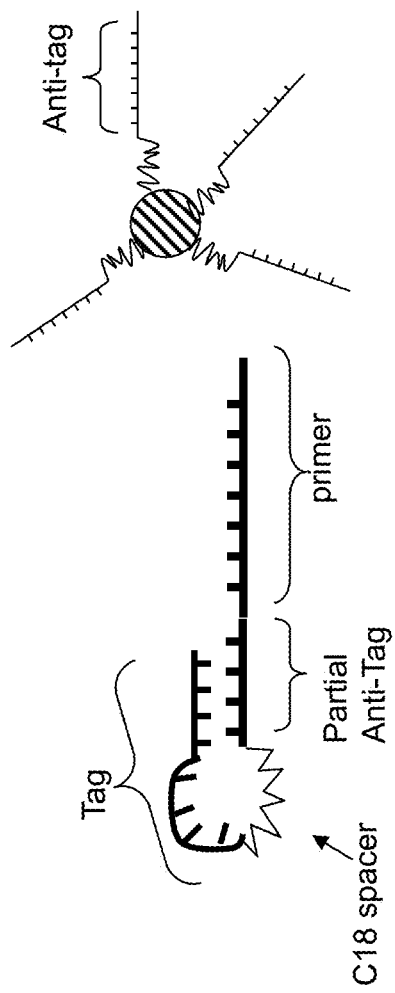
FIG. 1A shows an illustration of a hairpin-forming primer and a capture complex.
Figure 1B:
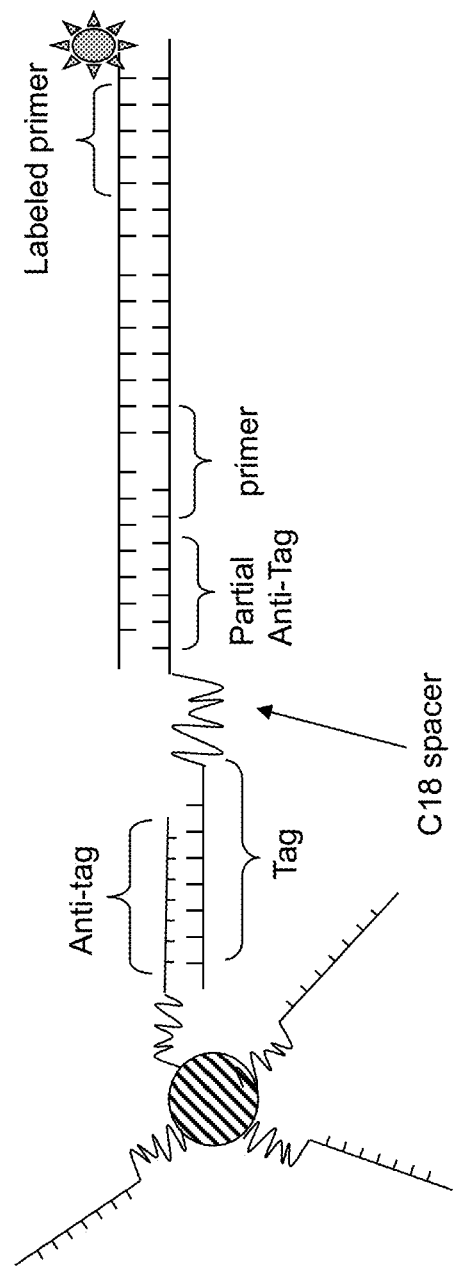
FIG. 1B shows an amplification product in which the amplification opened the structure of the hairpin-forming primer such that the tag region of the primer is able to hybridize to the anti-tag region of the capture complex.

In certain embodiments, the methods and compositions disclosed herein employ a hairpin-forming primer that, in addition to the target-specific primer sequence, comprises a tag region and a region that is complimentary to the tag region (anti-tag). The tag and anti-tag regions are separated by a blocker (to prevent polymerase extension into the tag region). These primers may also be referred to as being "chimeric" because they are composed of regions that serve different purposes. Prior to amplification, the tag and anti-tag regions hybridize forming a hairpin structure, thus sequestering the tag region. Once a double-stranded amplification product is formed, the hairpin stem structure is disrupted and the tag region becomes available to bind to another anti-tag probe, such as an anti-tag probe immobilized on a substrate (e.g., a bead). An example in which the hairpin-forming primer is the forward primer is illustrated in FIGS. 1A and 1B. It will be understood by those in the art that in an alternative embodiment the reverse primer could be the hairpin-forming primer.

As shown in FIG. 1A, the hairpin-forming forward primer comprises a target-specific primer region, an anti-tag region, a blocker region (a C18 spacer in this drawing), and a tag region. The anti-tag region of the primer can be the same length as the tag region or it can be a different length. In FIG. 1A the anti-tag region is shorter than its complementary tag region; thus it is referred to as a partial anti-tag region. Prior to polymerase extension and the creation of a double-stranded amplification product, the anti-tag region hybridizes with the tag region to form a hairpin structure, which prevents the tag region on the primer from hybridizing to the anti-tag region that is coupled to the bead. As shown in FIG.

1B, upon extension of the reverse primer, a polymerase with strand displacement activity will disrupt the hairpin stem and stop at the blocker allowing the tag region to hybridize to the anti-tag region on the bead.

Figure 2:
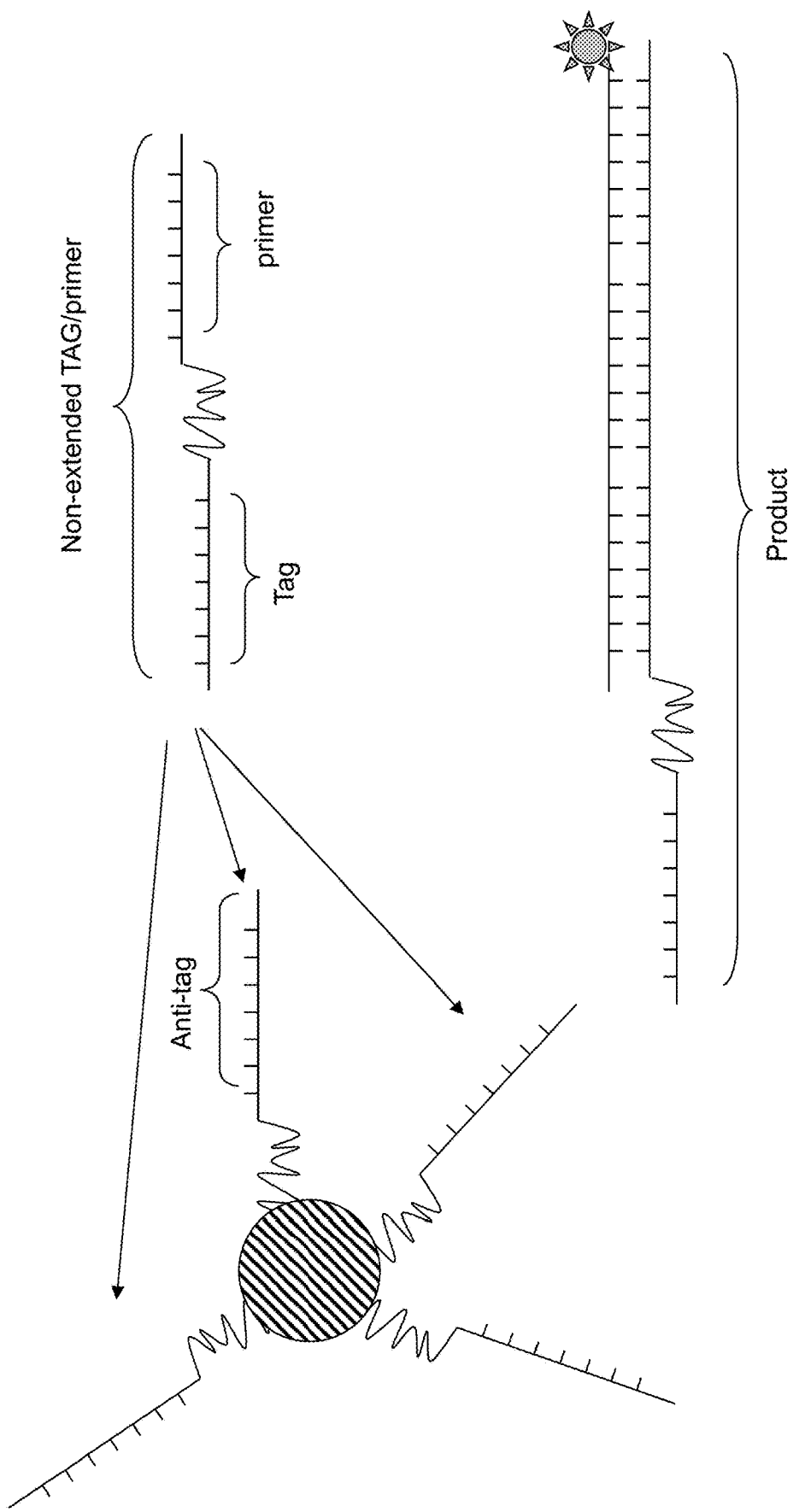
FIG. 2 illustrates how when non-hairpin-forming primers are used, the tag regions of non-extended primers can compete with the tag regions of the extended primers for hybridization to the anti-tag region of the capture complex.

Unextended forward primers will be inhibited from binding the immobilized anti-tag probes because of sequestration of the tag regions in a hairpin structure. This is advantageous because the occupation of hybridization sites on capture complexes by unextended primers can limit the availability of capture probes for labeled amplification product and thus decrease assay sensitivity. This is particularly problematic early in an amplification reaction due to the high ratio of unextended primers to extended primers at this stage. This effect is most significant when trying to measure accumulation of amplified product in real-time. As illustrated in FIG. 2A, excess unextended tagged primers that do not form hairpins can compete with the amplification products for hybridization sites on the capture complexes. Moreover, if intercalating or DNA binding dyes are used, they will bind to the double-stranded nucleic acid created by the hybridization of the unextended primer to the probe causing an increase in background signal. In contrast, when using primers with a hairpin structure, the primers and probes will not hybridize until a PCR amplification product is formed.

The use of primers as described above can provide at least the following benefits, as compared to the use of non-hairpin forming primers: (1) requires less optimization of primer concentration; (2) produces faster results because fewer PCR cycles are required to achieve detectable signal; (3) produces lower background and higher specific signal when using DNA binding dyes; (4) provides more sensitive detection in general; and (5) provides a more accurate representation of product/target concentration.

Figure 3A:
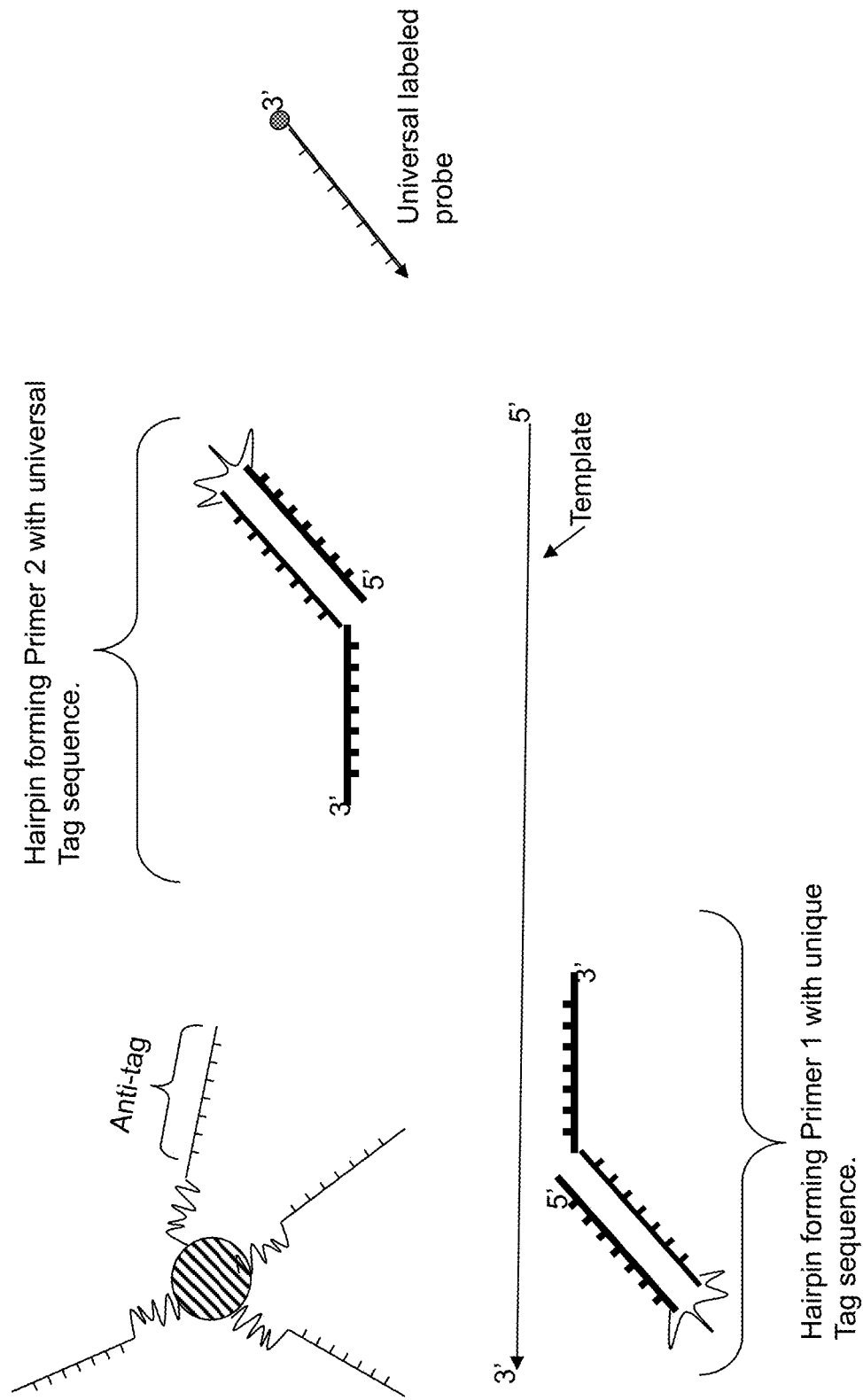
FIGS. 3A and 3B show a hairpin-forming forward primer, a hairpin-forming reverse primer, a labeled universal anti-tag molecule, and a capture complex before the amplification product is produced (FIG. 3A) and after the amplification product is produced (FIG. 3B).
Figure 3B:
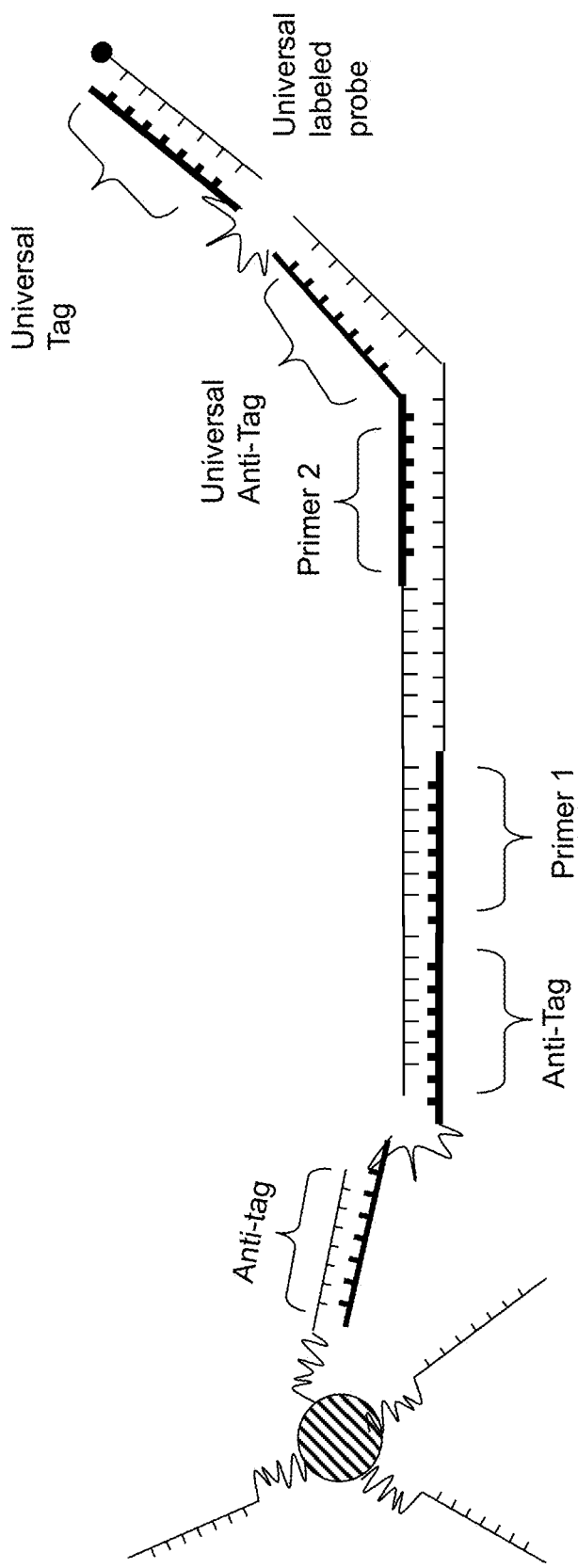
Figure 4A:
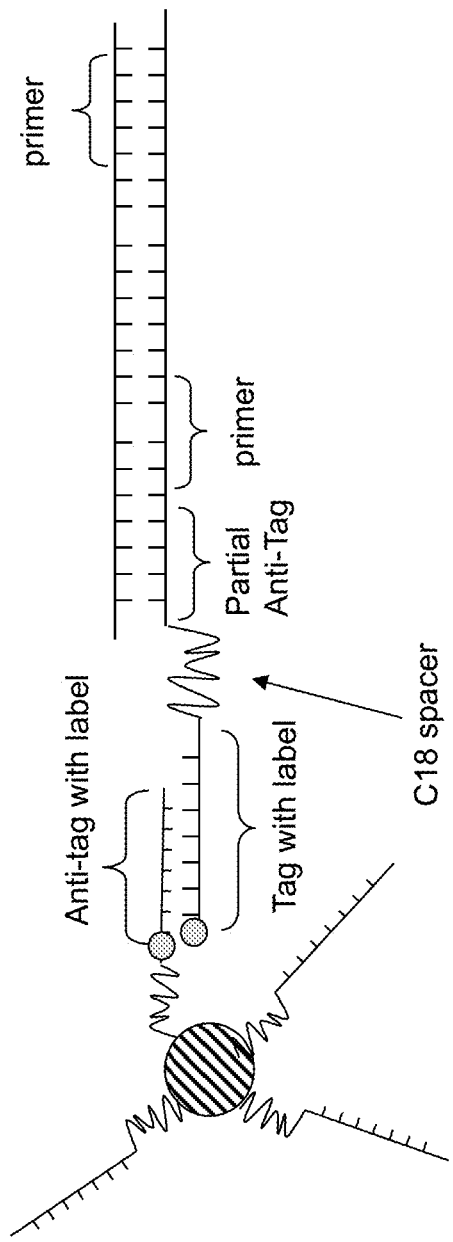
FIGS. 4A to 4E show various configurations of donor and acceptor chromophores in a FRET-based labeling system.
Figure 4B:
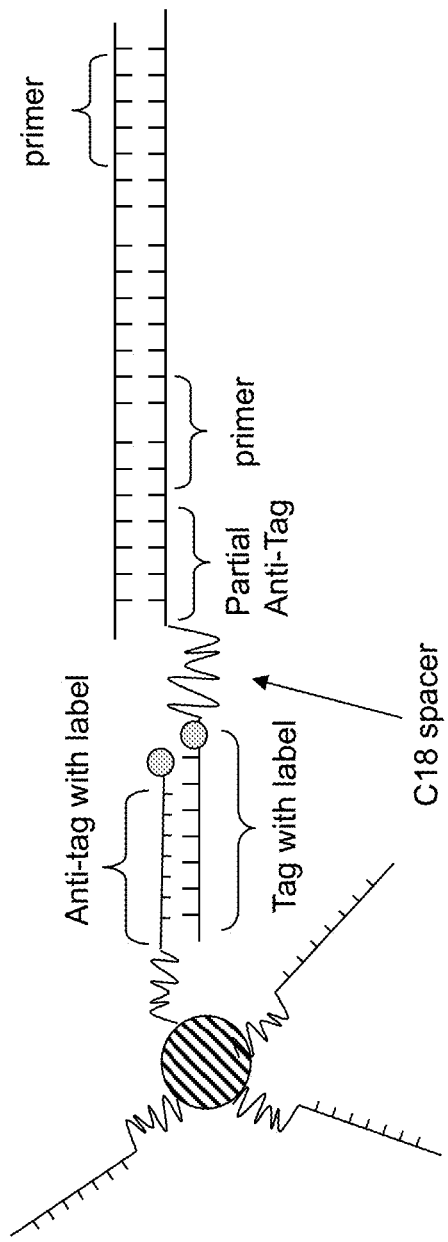
Figure 4C:
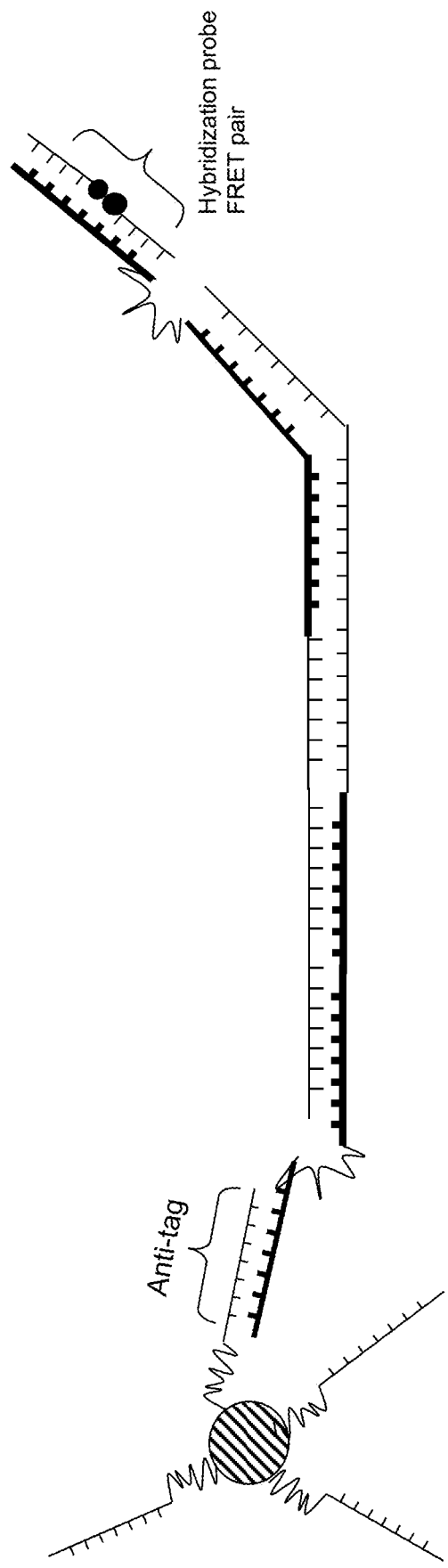
Figure 4D:
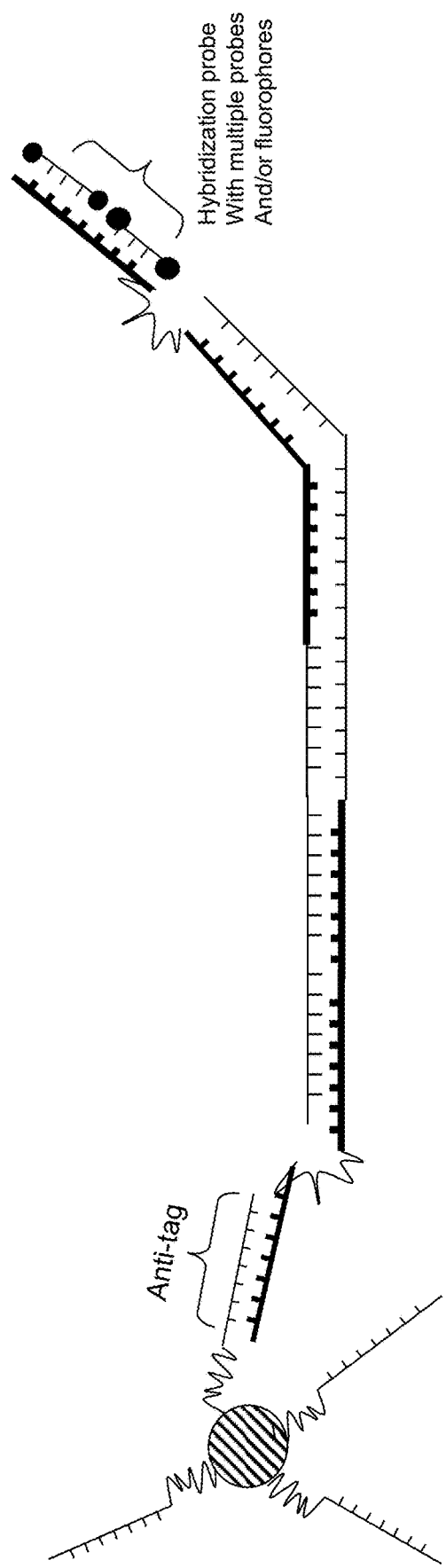
Figure 4E:
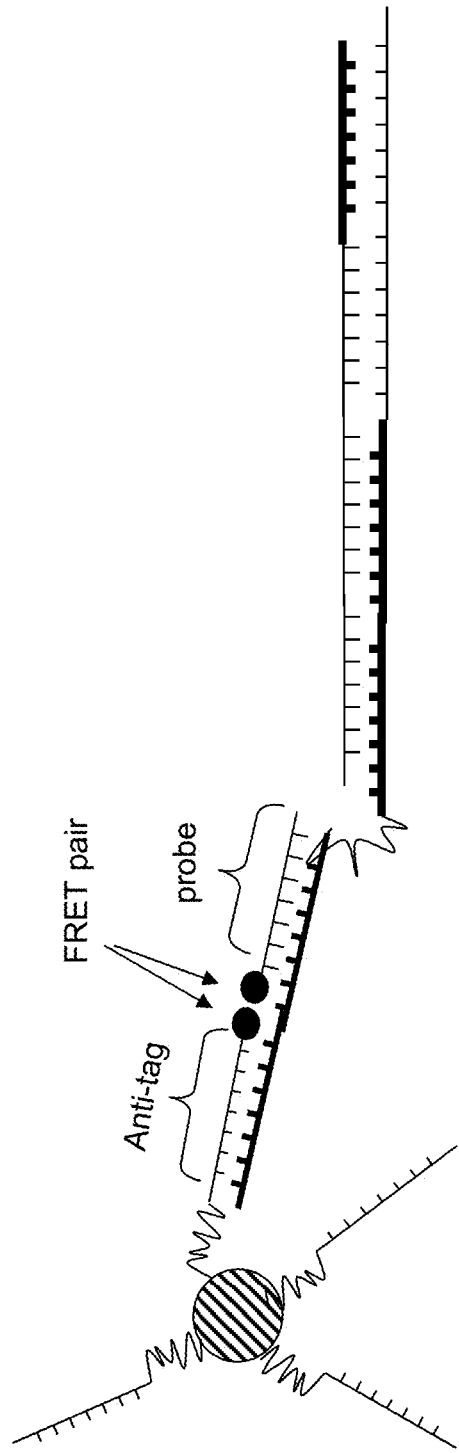

In certain embodiments, both the forward and the reverse primer of a primer pair are hairpin-forming primers. This can be particularly advantageous in multiplexed reactions. In this case, one of the primers of the primer pair comprises universal tag and anti-tag sequences. The tag and anti-tag sequences are "universal" because, while the target-specific primer sequence varies for each different target in the multiplexed amplification reaction, the same (i.e. "universal") tag and anti-tag sequences are used. An example illustrated in FIGS. 3A and 3B show a hairpin-forming forward primer comprising a target-specific primer region, and complementary anti-tag and tag regions separated by a blocker region. Also, shown is a hairpin-forming reverse primer comprising a target-specific primer region, and universal anti-tag and tag regions separated by a blocker region. The forward primer and reverse primer are designed such that they will prime the synthesis of a double-stranded nucleic acid during the polymerase chain reaction. In a multiplexed reaction, the anti-tag region and tag region of the forward primer are unique for each different forward primer in the reaction. In this way, amplification products of the extended forward primer can be identified by hybridization to a probe sequence. The universal anti-tag region and universal tag region, however, are the same for all reverse primers in the reaction. This allows the labeled, universal anti-tag probe to label all extended, reverse primers in the reaction. This greatly reduces the amount of label (e.g., fluorophore) required. For example, in a 30-plex PCR panel for infectious diseases in which 30 different reverse primers are directly labeled, 6,000 nM of fluorophore would be required, whereas only 200 nM of fluorophore would be required with a labeled, universal anti-tag. This is a 30× reduction in the amount of reporter required. These calculations are based on a 30-plex panel in which a sample is expected to test positive for 0 to 2 infectious agents. The ability to use less label reduces the background of the assay, reduces the amount of reagents needed, and can eliminate the need for a wash step to remove excess label from the assay.

B. Preparation of Nucleic Acids

The nucleic acids disclosed herein may be prepared by any technique known to one of ordinary skill in the art, such as for example, chemical synthesis, enzymatic production, or biological production. Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. Various different mechanisms of oligonucleotide synthesis have been disclosed in for example, U.S. Pat. Nos. 4,659,774, 4,816,571, 5,141,813, 5,264,566, 4,959, 463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al., 2001, incorporated herein by reference).

Nucleic acids used as a template for amplification may be isolated from cells, tissues or other samples according to standard methodologies (Sambrook et al., 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA (cDNA).

Depending upon the desired application, high stringency hybridization conditions may be selected that will only allow hybridization between sequences that are completely complementary. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

A reverse transcriptase PCR™ amplification procedure may be performed to reverse transcribe mRNA into cDNA. Methods of RT-PCR are well known in the art (see Sambrook et al., 2001). Alternative methods for RT-PCR utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of nucleic acid sequences that may be used in the practice of certain aspects of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence, which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids, which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA).

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR™" (Frohman, 1990; Ohara et al., 1989).

Amplification products may be visualized. If the amplification products are integrally labeled with radio- or fluorescent-labeled nucleotides, the amplification products can be exposed to x-ray film or visualized under the appropriate excitatory spectra. In another approach, a labeled nucleic acid probe is hybridized to the amplification product. The probe may be conjugated to, for example, a chromophore, fluorophore, radiolabel, or conjugated to a binding partner, such as an antibody or biotin.

Various nucleic acid detection methods known in the art are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

C. Hybridization

Sequence-specific nucleic acid hybridization assays are used for the detection of specific genetic sequences as indicators of genetic anomalies, mutations, and disease propensity. In addition, they are used for the detection of various biological agents and infectious pathogens. As used herein, "hybridization," "hybridizes" or "capable of hybridizing" is understood to mean the forming of a double or triple stranded molecule or a molecule with partial double or triple stranded nature. The term "anneal" as used herein is synonymous with "hybridize." The term "hybridization," "hybridizes" or "capable of hybridizing" encompasses the terms "stringent conditions" or "high stringency" and the terms "low stringency" or "low stringency conditions."

As used herein "stringent conditions" or "high stringency" are those conditions that allow hybridization between or within one or more nucleic acid strands containing complementary sequences, but preclude hybridization of non-complementary sequences. Such conditions are well known to those of ordinary skill in the art, and are preferred for applications requiring high selectivity. Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acids, the length and nucleobase content of the target sequences, the charge composition of the nucleic acids, and to the presence or concentration of formamide, tetramethylammonium chloride or other solvents in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Non-limiting examples of low stringency conditions include hybridization performed at about 0.15 M to about 0.9 M NaCl at a temperature range of about 20° C. to about 50° C. Of course, it is within the skill of one in the art to further modify the low or high stringency conditions to suit a particular application.

II. Detection of Nucleic Acids

A. Labels

To detect nucleic acids, it will be advantageous to employ nucleic acids in combination with an appropriate detection system. Recognition moieties incorporated into primers, incorporated into the amplified product during amplification, or attached to probes are useful in the identification of nucleic acid molecules. A number of different labels, also referred to as "reporters," may be used for this purpose such as fluorophores, chromophores, radiophores, enzymatic tags, antibodies, chemi/electroluminescent labels, affinity labels, etc. One of skill in the art will recognize that these and other labels not mentioned herein can be used with success in this invention. Examples of affinity labels include, but are not limited to the following: an antibody, an antibody fragment, a receptor protein, a hormone, biotin, digoxigen, DNP, or any polypeptide/protein molecule that binds to an affinity label.

Examples of enzyme tags include enzymes such as urease, alkaline phosphatase or peroxidase to mention a few. Colorimetric indicator substrates can be employed to provide a detection means visible to the human eye or spectrophotometrically, to identify specific hybridization with complementary nucleic acid-containing samples. All of these examples are generally known in the art and the skilled artisan will recognize that the invention is not limited to the examples described above.

Examples of fluorophores include, a red fluorescent squarine dye such as 2,4-Bis[1,3,3-trimethyl-2-indolinylidenemethyl] cyclobutenediylium-1,3-dioxolate, an infrared dye such as 2,4 Bis [3,3-dimethyl-2-(1H-benz[e] indolinylidenemethyl)] cyclobutenediylium-1,3-dioxolate, or an orange fluorescent squarine dye such as 2,4-Bis [3,5-dimethyl-2-pyrrolyl] cyclobutenediylium-1,3-diololate. Additional non-limiting examples of fluorophores include quantum dots, Alexa Fluor® dyes, AMCA, BODIPY® 630/650, BODIPY® 650/665, BODIPY®-FL, BODIPY®-R6G, BODIPY®-TMR, BODIPY®-TRX, Cascade Blue®, CyDye™, including but not limited to Cy2™, Cy3™, and Cy5™, a DNA intercalating dye, 6-FAM™, Fluorescein, HEX™, 6-JOE, Oregon Green® 488, Oregon Green® 500, Oregon Green® 514, Pacific Blue™, REG, phycobilliproteins including, but not limited to, phycoerythrin and allophycocyanin, Rhodamine Green™, Rhodamine Red™, ROX™ TAMRA™, TET™, Tetramethylrhodamine, or Texas Red®. A signal amplification reagent, such as tyramide (PerkinElmer), may be used to enhance the fluorescence signal.

It is contemplated that FRET-based detection systems may be used with the methods and compositions disclosed herein. FRET (fluorescence resonance energy transfer or Forster resonance energy transfer) makes use of the transfer of energy between donor and acceptor chromophores. In certain embodiments, a chromophore is attached to the hairpin sequence or the blocker and another chromophore is attached to the capture complex, such that upon attachment of the primer to the capture complex, an increase in signal will be observed by virtue of the energy transfer between the donor and acceptor chromophores. Various, non-limiting examples of the configurations of the donor and acceptor chromophores are shown in FIGS. 4A to 4E. FRET-based detection reduce background and therefore allow for higher multiplexing of primer sets compared to free floating chromophore methods, particularly in closed tube and real-time detection systems.

Figure 5A:
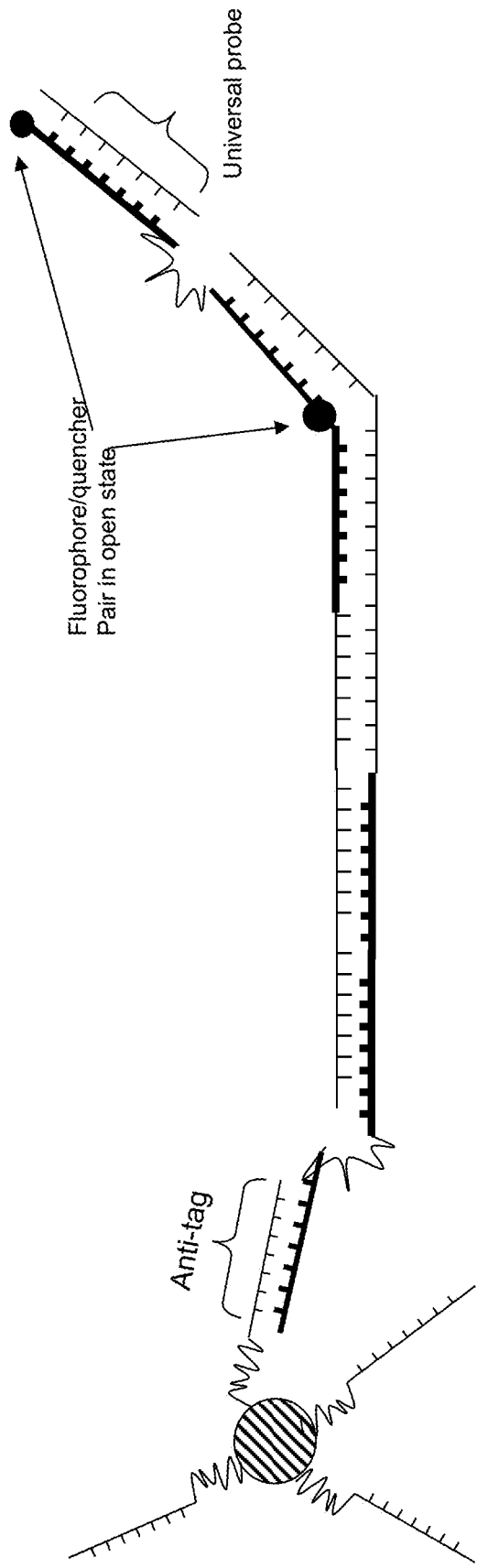
FIGS. 5A to 5B show various configurations of fluorophores and quenchers in a fluorophore/quencher-based labeling system.
Figure 5B:
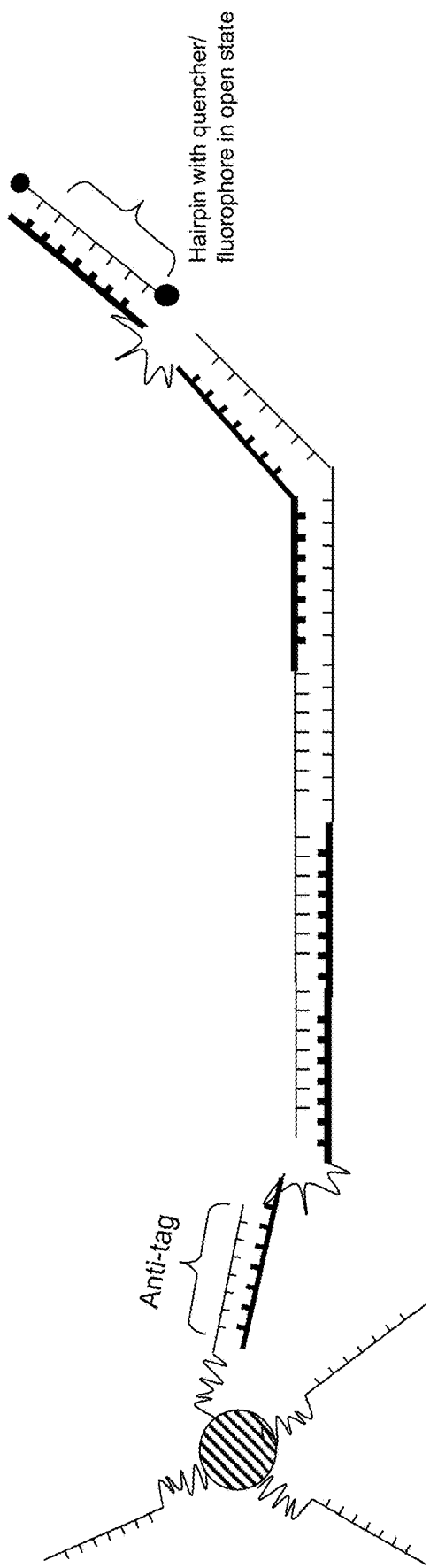

It is also contemplated that fluorophore/quencher-based detection systems may be used with the methods and compositions disclosed herein. When a quencher and fluorophore are in proximity to each other, the quencher quenches the signal produced by the fluorophore. A conformational change in the nucleic acid molecule separates the fluorophore and quencher to allow the fluorophore to emit a fluorescent signal. Various, non-limiting examples of the configurations of the fluorophore and quencher are shown in FIGS. 5A to 5B. Like FRET-based detection, fluorophore/quencher-based detection systems reduce background and therefore allow for higher multiplexing of primer sets compared to free floating fluorophore methods, particularly in closed tube and real-time detection systems.

B. Gene Chips and Microarrays

Certain embodiments of the present invention involve a solid support. The solid support may be a planar array, such as a gene chip or microarray. Arrays and gene chip technology provide a means of rapidly screening a large number of nucleic acid samples for their ability to hybridize to a variety of single stranded oligonucleotide probes immobilized on a solid substrate. These techniques involve quantitative methods for analyzing large numbers of genes rapidly and accurately. The technology capitalizes on the complementary binding properties of single stranded DNA to screen DNA samples by hybridization (Pease et al., 1994; Fodor et al., 1991). Basically, an array or gene chip consists of a solid substrate upon which an array of single stranded DNA or RNA molecules have been attached. For screening, the chip or array is contacted with a single stranded DNA or RNA sample, which is allowed to hybridize under stringent conditions. The chip or array is then scanned to determine which probes have hybridized. The identity of the probes on the chip or planar array is known by its spatial location (i.e., x, y coordinate) on the chip or planar array.

The ability to directly synthesize on or attach polynucleotide probes to solid substrates is well known in the art. See U.S. Pat. Nos. 5,837,832 and 5,837,860, both of which are expressly incorporated by reference. A variety of methods have been utilized to either permanently or removably attach the probes to the substrate. Exemplary methods include: the immobilization of biotinylated nucleic acid molecules to avidin/streptavidin coated supports (Holmstrom, 1993), the direct covalent attachment of short, 5'-phosphorylated primers to chemically modified polystyrene plates (Rasmussen et al., 1991), or the precoating of the polystyrene or glass solid phases with poly-L-Lys or poly L-Lys, Phe, followed by the covalent attachment of either amino- or sulfhydryl-modified oligonucleotides using bi-functional crosslinking reagents (Running et al., 1990; Newton et al., 1993). When immobilized onto a substrate, the probes are stabilized and therefore may be used repeatedly. In general terms, hybridization is performed on an immobilized nucleic acid target or a probe molecule that is attached to a solid surface such as nitrocellulose, nylon membrane or glass. Numerous other matrix materials may be used, including reinforced nitrocellulose membrane, activated quartz, activated glass, polyvinylidene difluoride (PVDF) membrane, polystyrene substrates, polyacrylamide-based substrate, other polymers such as poly(vinyl chloride), poly(methyl methacrylate), poly(dimethyl siloxane), photopolymers (which contain photoreactive species such as nitrenes, carbenes and ketyl radicals capable of forming covalent links with target molecules.

C. Bead Arrays

In some embodiments, the solid support may be a microsphere. Microsphere-based assays may also be analyzed by technologies known to those in the art. For example, in certain embodiments, Luminex xMAP® technology may be used. The Luminex technology allows the detection of nucleic acid products immobilized on fluorescently encoded microspheres. By dyeing microspheres with 10 different intensities of each of two spectrally distinct fluorochromes, 100 fluorescently distinct populations of microspheres are produced. These individual populations (sets) can represent individual detection sequences and the magnitude of hybridization on each set can be detected individually. The magnitude of the hybridization reaction is measured using a third reporter, which is typically a third spectrally distinct fluorophore. The reporter molecule signals the extent of the reaction by attaching to the molecules on the microspheres. As both the microspheres and the reporter molecules are labeled, digital signal processing allows the translation of signals into real-time, quantitative data for each reaction. The Luminex technology is described, for example, in U.S. Pat. Nos. 5,736,330, 5,981,180, and 6,057,107, all of which are specifically incorporated by reference.

Flow cytometry can be used for simultaneous sequence identification and hybridization quantification in microsphere-based assays. Internal dyes in the microspheres are detected by flow cytometry and used to identify the specific nucleic acid sequence to which a microsphere is coupled. The label on the target nucleic acid molecule is also detected by flow cytometry and used to quantify target hybridization to the microsphere. Methods of flow cytometry are well know in the art and are described, for example, in U.S. Patents, all of which are specifically incorporated by reference. 5,981,180; 4,284,412; 4,989,977; 4,498,766; 5,478,722; 4,857,451; 4,774,189; 4,767,206; 4,714,682; 5,160,974; and 4,661,913

Microspheres may also be analyzed on array platforms that image beads and analytes distributed on a substantially planar array. In this way, imaging of bead arrays is similar to the gene chips discussed above. However, in contrast to gene chips where the analyte is identified by its spatial position on the array, bead arrays typically identify the analyte by the encoded microsphere to which it is bound. Examples of commercially available bead array systems include Illumina's BeadXpress™ Reader and BeadStation 500™.

D. Competitive Binding Assays

Embodiments of the present invention may also be used in conjunction with a competitive binding assay format. In general, this format involves a sequence coupled to a solid surface, and a labeled sequence, which is complementary to the sequence coupled to the solid surface, in solution. With this format, the target sequence in the sample being assayed does not need to be labeled. Rather, the target sequence's presence in the sample is detected because it competes with the labeled complement for hybridization with the immobilized detection sequence. Thus, if the target sequence is present in the sample, the signal decreases as compared to a sample lacking the target sequence. The Luminex xMAP technology described above can be used in a competitive binding assay format. The use of the Luminex technology in a competitive binding assay format is described in U.S. Pat. Nos. 5,736,330 and 6,057,107, incorporated herein by reference.

E. Tag Sequences

As mentioned above, various aspects of the present invention use complementary tag sequences (i.e., tags and anti-tags). A number of approaches have been developed that involve the use of oligonucleotide tags attached to a solid support that can be used to specifically hybridize to their tag complements that are coupled to primers, probe sequences, target sequences, etc. The proper selection of non-cross hybridizing tag and anti-tag sequences is useful in assays, particularly assays in a highly parallel hybridization environment, that require stringent non-cross hybridizing behavior.

Certain thermodynamic properties of forming nucleic acid hybrids are considered in the design of tag and anti-tag sequences. The temperature at which oligonucleotides form duplexes with their complementary sequences known as the $T_m$ (the temperature at which 50% of the nucleic acid duplex is dissociated) varies according to a number of sequence dependent properties including the hydrogen bonding energies of the canonical pairs A-T and G-C (reflected in GC or base composition), stacking free energy and, to a lesser extent, nearest neighbor interactions. These energies vary widely among oligonucleotides that are typically used in hybridization assays. For example, hybridization of two probe sequences composed of 24 nucleotides, one with a 40% GC content and the other with a 60% GC content, with its complementary target under standard conditions theoretically may have a 10° C. difference in melting temperature (Mueller et al., 1993). Problems in hybridization occur when the hybrids are allowed to form under hybridization conditions that include a single hybridization temperature that is not optimal for correct hybridization of all oligonucleotide sequences of a set. Mismatch hybridization of non-complementary probes can occur forming duplexes with measurable mismatch stability (Santalucia et al., 1999). Mismatching of duplexes in a particular set of oligonucleotides can occur under hybridization conditions where the mismatch results in a decrease in duplex stability that results in a higher $T_m$ than the least stable correct duplex of that particular set. For example, if hybridization is carried out under conditions that favor the AT-rich perfect match duplex sequence, the possibility exists for hybridizing a GC-rich duplex sequence that contains a mismatched base having a melting temperature that is still above the correctly formed AT-rich duplex. Therefore, design of families of oligonucleotide sequences that can be used in multiplexed hybridization reactions must include consideration for the thermodynamic properties of oligonucleotides and duplex formation that will reduce or eliminate cross hybridization behavior within the designed oligonucleotide set.

There are a number of different approaches for selecting tag and anti-tag sequences for use in multiplexed hybridization assays. The selection of sequences that can be used as zip codes or tags in an addressable array has been described in the patent literature in an approach taken by Brenner and co-workers (U.S. Pat. No. 5,654,413, incorporated herein by reference). Chetverin et al. (WO 93/17126, U.S. Pat. Nos. 6,103,463 and 6,322,971, incorporated herein by reference) discloses sectioned, binary oligonucleotide arrays to sort and survey nucleic acids. These arrays have a constant nucleotide sequence attached to an adjacent variable nucleotide sequence, both bound to a solid support by a covalent linking moiety. Parameters used in the design of tags based on subunits are discussed in Barany et al. (WO 9731256, incorporated herein by reference). A multiplex sequencing method has been described in U.S. Pat. No. 4,942,124, incorporated herein by reference. This method uses at least two vectors that differ from each other at a tag sequence.

U.S. Pat. No. 7,226,737, incorporated herein by reference, describes a set of 210 non-cross hybridizing tags and anti-tags. U.S. Published Application No. 2005/0191625, incorporated herein by reference, discloses a family of 1168 tag sequences with a demonstrated ability to correctly hybridize to their complementary sequences with minimal cross hybridization.

A population of oligonucleotide tag or anti-tag sequences may be conjugated to a population of primers or other polynucleotide sequences in several different ways including, but not limited to, direct chemical synthesis, chemical coupling, ligation, amplification, and the like. Sequence tags that have been synthesized with primer sequences can be used for enzymatic extension of the primer on the target for example in PCR amplification. A population of oligonucleotide tag or anti-tag sequences may be conjugated to a solid support by, for example, surface chemistries on the surface of the support.

8. Blocker Moieties

Blocker moieties prevent the polymerase from extending through the tag sequence region during second strand synthesis, thus allowing the tag sequence to remain single-stranded during amplification and therefore free to hybridize to its complementary anti-tag sequence in the capture complex.

A blocker moiety refers to any moiety that when linked (e.g., covalently linked) between a first nucleotide sequence and a second nucleotide sequence is effective to inhibit and preferably prevent extension of either the first or second nucleotide sequence but not both the first and second nucleotide sequence. There are a number of molecules that may be used as blocker moieties. Non-limiting examples of blocker moieties include C6-20 straight chain alkylenes and iSp18 (which is an 18-atom hexa-ethyleneglycol). Blocker moieties may include, for example, at least one deoxy ribofuranosyl naphthalene or ribofuranosyl naphthalene moiety, which may be linked to the adjacent nucleotides via a 3'-furanosyl linkage or preferably via a 2'-furanosyl linkage. A blocker moiety may be an oligonucleotide sequence that is in the opposite orientation as the target specific sequence. Various blocker moieties and their use are described in U.S. Pat. No. 5,525,494, which is incorporated herein by reference.

III. Examples

The following examples are included to demonstrate certain embodiments of the invention. Those of skill in the art should, in light of the present disclosure, will appreciate that many changes can be made in the specific embodiments that are disclosed and still obtain a like or similar result without departing from the spirit and scope of the invention.

A. Example 1

A side by side study was performed to compare hairpin-forming primers comprising tag and anti-tag regions with non-hairpin forming primers comprising a tag region but not an anti-tag region. These "tagged" primers were used as forward primers. Cy3-labeled reverse primers (400 nM) were added along with the respective forward primer (hairpin forming or non-hairpin forming) as well as a detection bead prior to PCR amplification. The target was a thrombophilia gene, MTHFR Exon 7. After 27 cycles, the samples were analyzed on an LX200 (Luminex Corp.) at room temperature without any other addition of buffer or reporter, thus representing a simulated closed-tube detection format.

The forward primers were:

```
12snap:
                                       (SEQ ID NO: 1)
5'CAAACAAACATTCAAATATCAATC/iSp18/CTATCTATACATAATGT

TTGTTTGCAAGGAGGAGCTGCTGAAGATG3'

12isoSNAP:
                                       (SEQ ID NO: 2)
5'CAAACAAACATTCAAATATCAATC/ie-isodC//iMeisodC/CTAT

CTATACATAATGTTTGTTTGCAAGGAGGAGCTGCTGAAGATG3'.

Snap1:
                                       (SEQ ID NO: 3)
5'CAAACAAACATTCAAATATCAATC/iSp18/GATTGATATTGAATGTT

TGTTTGCAAGGAGGAGCTGCTCAACATG3'

NoSnap
                                       (SEQ ID NO: 4)
5'CAAACAAACATTCAAATATCAATC/iSp18/CTATCTATACATTTACA

AACATTCCAAGGAGGAGCTGCTGAAGATG3'

TIF
                                       (SEQ ID NO: 5)
5'CAAACAAACATTCAAATATCAATC/iSp18/CAAGGAGGAGCTGCTCA

ACATG3'
```

The sequence of the Cy3-labeled reverse primer was:

```
                                       (SEQ ID NO: 6)
/5Cy3/CACTTTGTGACCATTCCGGTTTG
```

12snap and 12isoSNAP differed from each other in that 12snap contains an iSp18 blocker and 12isoSNAP contains an isodC blocker. The 12snap and 12isoSNAP were calculated to be in the hairpin conformation 99.9% of the time in solution (37° C.; [monovalent]=0.0500 mol/L; [Mg$^{2+}$]=0.0015 mol/L; [Betaine]=1.00 mol/L) by Visual OMP software. Snap1 was similar to 12snap except that it had 24-base tag hybridizing to its complimentary anti-tag in the hairpin, rather than 12 bases as in 12snap. NoSnap was as long as 12snap but without a hairpin structure. The TIF primer included a tag sequence but no complementary anti-tag sequence.

All PCR reactions were performed in the same cocktail. These were analyzed after 27 cycles of amplification and 36 cycles of amplification. A PCR cocktail was prepared using the following concentrations and reagents:

TABLE 1

| | 1x Volume | |
|---|---|---|
| Master Mix | 25 µl | HotStart TAQ Plus Master Mix 2X (Qiagen) |
| H$_2$O | 21 µl | RNASE FREE Water (Qiagen) |
| Primer | 1 µl | IDT (400 nM final concentration each) |
| Template | 1 µl | Purified Human DNA Sample from UCLA (100 ng) |
| Beads | 2 µl | MagPlex Microspheres (Luminex) (5000 per set) |
| Total | 50 µl | |

These formulations were used along with the downstream primer:

```
                                       (SEQ ID NO: 7)
LUA-MED-TF/5Cy3/CACTTTGTGACCATTCCGGTTTG.
```

Each primer was at 400 nM concentration. The cycling conditions for this reaction were as follows:

Heat Denaturation Step; 95° C. for 5 min.

Cycling Steps (for 36 cycles): 94° C. for 30 s, 55° C. for 30 s, 72° C. for 30 s.

After amplification the reactions were stored until all reactions were completed and were then placed in a v-bottom plate and analyzed on a Luminex 200 analyzer after 3 minutes at 96° C. and 12 minutes at 37° C.

Results are shown in Table 2 below. Analyte 27 is the positive bead set with the anti-tag region coupled to the bead. Analyte 33 is the negative control with a non-specific sequence coupled to the bead. Median values are shown.

TABLE 2

| Location | Sample | Analyte 27 MFI | Analyte 33 MFI | Cycles |
|---|---|---|---|---|
| 1(1, A1) | 12isoSNAP | 77 | 11 | 36 |
| 2(1, B1) | 12isoSNAP | 86 | 4 | |
| 3(1, C1) | 12snap | 113 | 14 | |
| 4(1, D1) | 12snap | 120 | 9.5 | |
| 5(1, E1) | NoSnap | 107 | 13 | |
| 6(1, F1) | NoSnap | 111.5 | 9.5 | |
| 7(1, G1) | snap1 | 98.5 | 10 | |
| 8(1, H1) | snap1 | 98.5 | 8 | |
| 9(1, A2) | TIF | 118 | 12 | |

TABLE 2-continued

| Location | Sample | Analyte 27 MFI | Analyte 33 MFI | Cycles |
|---|---|---|---|---|
| 10(1, B2) | TIF | 108 | 15 | |
| 11(1, C2) | TIF | 36 | 10.5 | 27 |
| 12(1, D2) | TIF | 32.5 | 7 | |
| 13(1, E2) | snap1 | 24.5 | 7 | |
| 14(1, F2) | snap1 | 21 | 13.5 | |
| 15(1, G2) | NoSnap | 20 | 8 | |
| 16(1, H2) | NoSnap | 26.5 | 12.5 | |
| 17(1, A3) | 12snap | 58 | 12 | |
| 18(1, B3) | 12snap | 53 | 15.5 | |
| 19(1, C3) | 12isoSNAP | 25 | 9 | |
| 20(1, D3) | 12isoSNAP | 31.5 | 13 | |

The high signal (MFIs of 58 and 53) from the 12snap primer at the $27^{th}$ cycle as compared to the signal (MFIs of 20 and 26.5) from the NoSnap primer indicates that the 12snap primer is folding when it is supposed to and not interfering with hybridization at the stage of the reaction where excess primer would be expected.

B. Example 2

Another study was performed in which after amplification to 27 cycles as described in Example 1, the samples were spiked with more of the same forward primer (400 nM) that they were originally amplified with. Addition of excess primer prior to hybridization, but after amplification, was done to test whether the non-extended hairpin primers were interfering with hybridization to the bead, and whether the TIF primers were interfering with hybridization. If there was interference, one would expect that the spiked primers would decrease the MFI value.

TABLE 3

| Location | Sample | Analyte 27 MFI | Analyte 33 MFI | Total Events |
|---|---|---|---|---|
| 1(1, A1) | TIF | 91.5 | 8 | 203 |
| 2(1, B1) | TIF | 94 | 5.5 | 201 |
| 3(1, C1) | 12snap | 115.5 | 11 | 211 |
| 4(1, D1) | 12snap | 119 | 8 | 206 |
| 5(1, E1) | TIF spiked 400 nM | 63 | 13.5 | 208 |
| 6(1, F1) | TIF spiked 400 nM | 64 | 8.5 | 208 |
| 7(1, G1) | 12snap spiked 400 nM | 106 | 13 | 207 |
| 8(1, H1) | 12snap spiked 400 nM | 109 | 15 | 203 |

Figure 6:
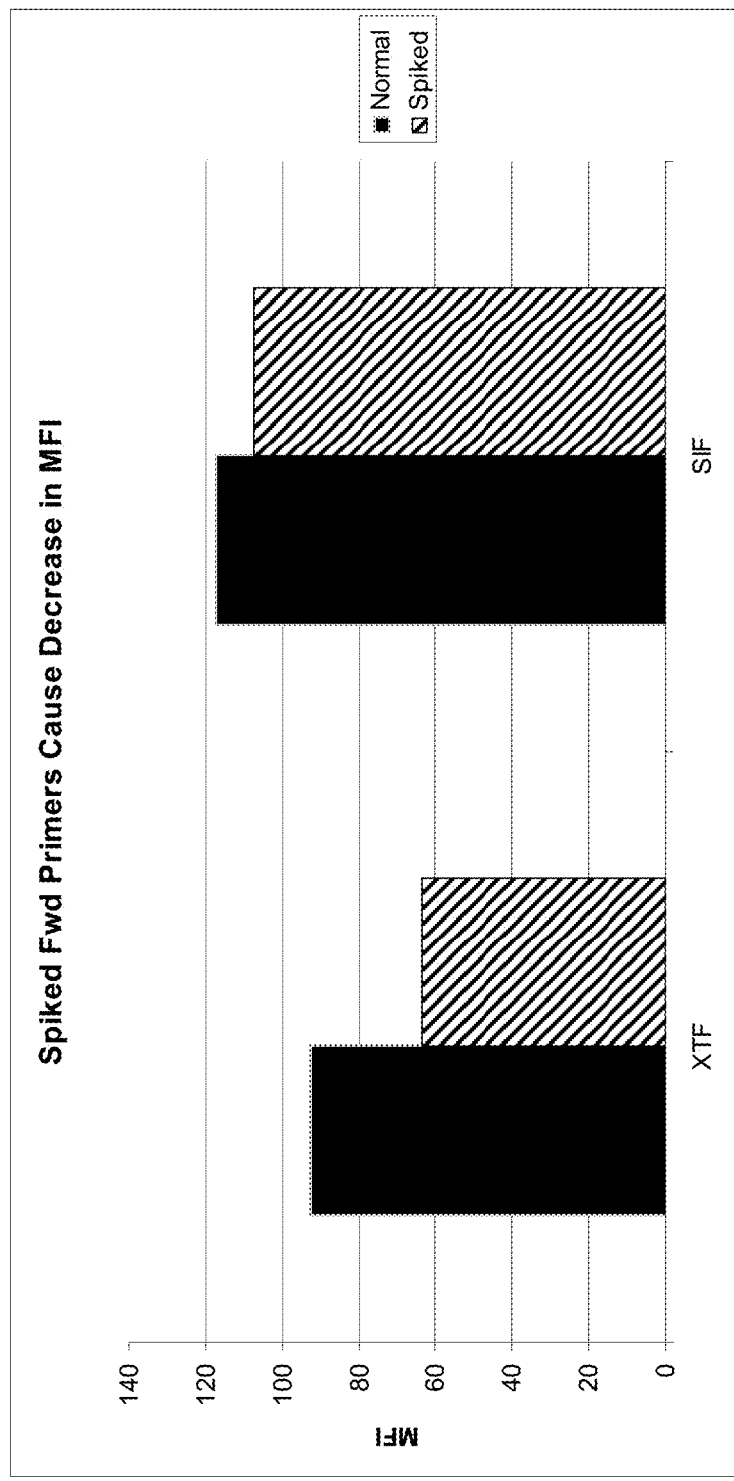
FIG. 6 is a graph showing that hairpin primers are more effective in the presence of excess, non-extended primers than are primers that do not form hairpins.

As shown in Table 3 and FIG. 6, the MFI for the TIF primer sample dropped to 68% of its original value when excess TIF primer was added, whereas the 12snap primer only dropped to 92% of its original value when excess 12snap primer was added. The slight drop in signal observed with the 12snap primer could be due to incomplete hairpin structure formation by these primers, as only 12 base pairs are available for hairpin formation.

C. Example 3

Varying amounts of primer concentration were tested in PCR reactions stopped at 27 cycles to determine whether the signal would increase or decrease with additional amounts of TIF primer or 12snap primer. The results are shown in Tables 4 and 5 below.

TABLE 4

| | 12snap primer | | | |
|---|---|---|---|---|
| Location | Primer Concentration | Analyte 27 MFI | Analyte 33 MFI | Total Events |
| 1(1, A1) | 100 nM | 96 | 4 | 213 |
| 2(1, B1) | 100 nM | 99 | 4 | 203 |
| 3(1, C1) | 100 nM | 101.5 | 7 | 211 |
| 4(1, D1) | 200 nM | 111.5 | 8 | 220 |
| 5(1, E1) | 200 nM | 103 | 7 | 212 |
| 6(1, F1) | 200 nM | 108 | 10 | 200 |
| 7(1, G1) | 400 nM | 121 | 12 | 206 |
| 8(1, H1) | 400 nM | 114 | 8 | 205 |
| 9(1, A2) | 400 nM | 118.5 | 14.5 | 214 |

TABLE 5

| | TIF primer | | | |
|---|---|---|---|---|
| Location | Primer Concentration | Analyte 27 MFI | Analyte 33 MFI | Total Events |
| 1(1, A1) | 100 nM | 53 | 2 | 234 |
| 2(1, B1) | 100 nM | 63.5 | 5 | 214 |
| 3(1, C1) | 100 nM | 62 | 3.5 | 206 |
| 4(1, D1) | 200 nM | 60 | 5.5 | 209 |
| 5(1, E1) | 200 nM | 63 | 11 | 207 |
| 6(1, F1) | 200 nM | 62 | 7.5 | 216 |
| 7(1, G1) | 400 nM | 55 | 13 | 209 |
| 8(1, H1) | 400 nM | 43 | 8.5 | 209 |
| 9(1, A2) | 400 nM | 52 | 14 | 203 |

The data show that one can gain greater signal with the hairpin primer by increasing the concentration, whereas greater signal cannot be obtained by increasing the TIF primer. This indicates that the hairpin primer does not interfere as much with hybridization to the bead as does the TIF primer.

D. Example 4

Two additional studies were performed to confirm: (1) that the Cy3-labeled reverse primer was not hybridizing to the forward primers; and (2) that primer dimers were not forming.

The primers (the Cy3-labeled reverse primer and either 12snap or TIF) were mixed with the anti-tagged beads in PCR solution and heated to 96° C. for 3 minutes followed by 37° C. for 12 minutes. As shown in Table 6, no non-specific binding of the reverse primer to either forward primer was detected.

TABLE 6

| Location | Sample | Analyte 27 MFI | Analyte 33 MFI | Total Events |
|---|---|---|---|---|
| 1(1, A1) | 12snap | 14.5 | 24.5 | 204 |
| 2(1, B1) | 12snap | 12 | 14 | 204 |
| 3(1, C1) | no forward primer | 3 | 3.5 | 203 |
| 4(1, D1) | TIF | 12 | 10.5 | 205 |
| 5(1, E1) | TIF | 11 | 6 | 215 |
| 6(1, F1) | no forward primer | 2 | 2.5 | 200 |

PCR reactions with the upstream primers 12snap and TIF and the Cy3-labeled reverse primer were performed in the absence of template to check for the formation of primer dimers. The reactions were run in duplicate on RD18 after a 3 minute 96° C. and 12 minute 37° C. hyb protocol. The results shown in Table 7 indicate that no primer dimers were formed and hybridized to the beads.

TABLE 7

| Location | Sample | Analyte 27 MFI | Analyte 33 MFI | Total Events |
|---|---|---|---|---|
| 1(1, A1) | TIF, no template | 0.5 | 2 | 205 |
| 1(1, B1) | TIF, no template | 0.5 | 0 | 209 |
| 6(1, F1) | 12snap, no template | 5 | 0.5 | 203 |
| 5(1, E1) | 12snap, no template | 2 | 0 | 212 |
| 9(1, A2) | TIF | 102.5 | 0 | 200 |
| 10(1, B2) | TIF | 104 | 0 | 207 |
| 14(1, F2) | 12snap | 132 | 3.5 | 208 |
| 13(1, E2) | 12snap | 120 | 0 | 224 |

E. Example 5

Forward primers that formed 16-mer and 14-mer stem structures in the hairpins were also studied. An additional tagged, but non-hairpin forming primer, TIF, was also included in these studies.

```
16snap:
                                              (SEQ ID NO: 8)
CAA ACA AAC ATT CAA ATA TCA ATC /iSp18/CTC TCT ATT

TTG AAT GTT TGT TTG CAA GGA GGA GCT GCT GAA GAT G

14snap:
                                              (SEQ ID NO: 9)
CAA ACA AAC ATT CAA ATA TCA ATC /iSp18/CTC AAC TAT

TTT GAA TGT TTG TTT GCA AGG AGG AGC TGC TGA AGA TG
```

16snap and 14snap were tested in PCR reactions and in PCR solution using oligos complimentary to the primer region. The following PCR set up was designed to test the oligos in Qiagen Hotstart Master Mix with no extra $MgCl_2$ added.

TABLE 8

| Master Mix | 25 µl |
|---|---|
| $H_2O$ | 19.75 µl |
| Primer | 2 µl |
| Template | 0.25 µl |
| Beads (2) | 3 µl |
| Total | 50 µl |

The reaction was stopped at 27 cycles and hybridized for 2 minutes at 96° C. followed by 37° C. for 12 minutes. The results were as follows:

TABLE 9

| Location | Sample | Analyte 27 MFI | Analyte 33 MFI |
|---|---|---|---|
| 1(1, A1) | 16snap | 33 | 0 |
| 2(1, B1) | 16snap | 34 | 1 |
| 3(1, C1) | 16snap | 35 | 2 |
| 4(1, E1) | 14snap | 32 | 2 |
| 5(1, F1) | 14snap | 31 | 0 |
| 6(1, G1) | 14snap | 34.5 | 3.5 |
| 7(1, A2) | 12snap | 52.5 | 3 |
| 8(1, B2) | 12snap | 59 | 0 |
| 9(1, C2) | 12snap | 62.5 | 1 |
| 10(1, E2) | TIF | 47.5 | 0 |
| 11(1, F2) | TIF | 47 | 0 |
| 12(1, G2) | TIF | 48 | 2 |

Figure 7:
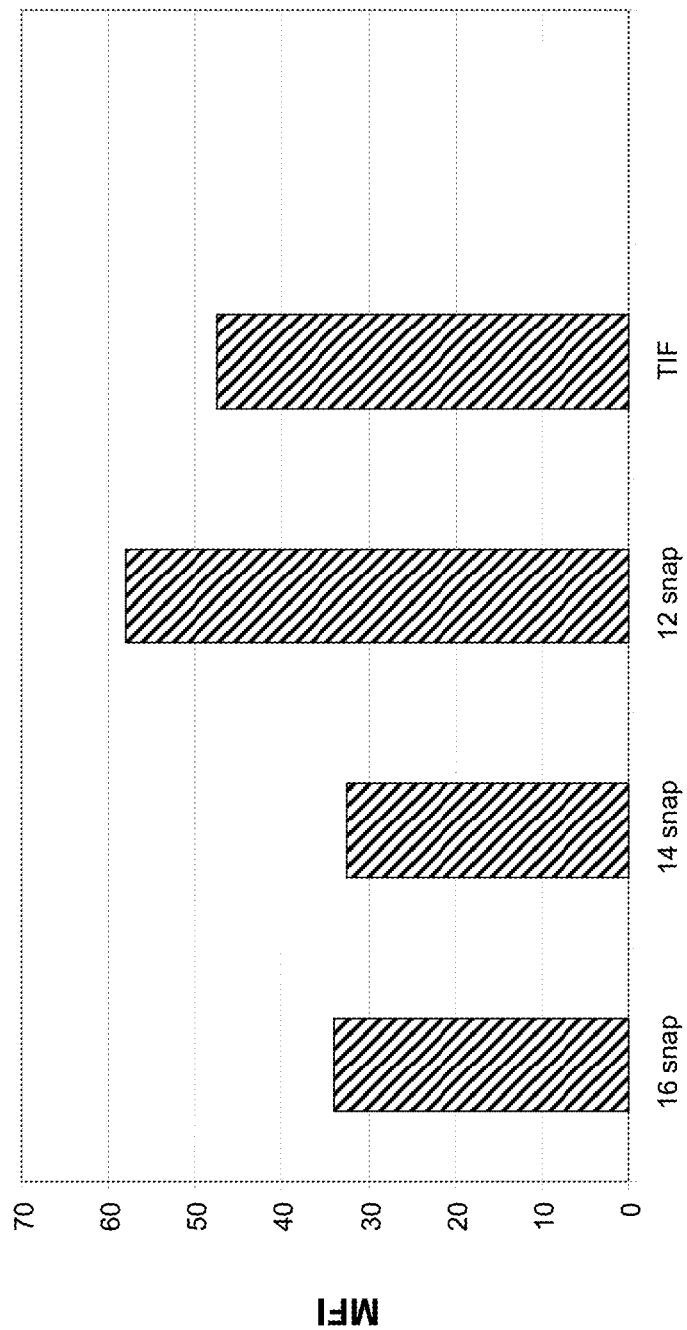
FIG. 7 is a graph showing a comparison of 12-, 14-, and 16-mer stem hairpin primers, and non-hairpin forming primers (TIF), in a PCR with Qiagen HotStart polymerase.

The data from Table 9 is also represented graphically in FIG. 7. The 16snap and 14snap primers produced lower signals than 12snap. They also produced lower signals than TIF. It was postulated that the exonuclease activity of the polymerase in the Qiagen Hotstart Master Mix was degrading the stem structure on the 16snap and 14snap primers. Accordingly, another PCR, which was also stopped at 27 cycles, was performed using the exo (−) polymerase apta taq. The cocktail for this PCR was as follows:

TABLE 10

| 10x Buffer | 5 µl |
|---|---|
| $H_2O$ | 29.5 µl |
| Primer | 4 µl |
| Template | 0.25 µl |
| Beads (2) | 2 µl |
| dNTPs | 1 µl |
| apta taq | 0.25 µl |
| $MgCl_2$ | 8 µl |
| Total | 50 µl |

The results of the reaction with apta taq were as follows:

TABLE 11

| Location | Sample | Analyte 27 MFI | Analyte 33 MFI |
|---|---|---|---|
| 1(1, A1) | 16snap | 98 | 0 |
| 2(1, B1) | 16snap | 99 | 2 |
| 3(1, C1) | 16snap | 94 | 4 |
| 4(1, D1) | 16snap | 106 | 2 |
| 5(1, E1) | 14snap | 133 | 0 |
| 6(1, F1) | 14snap | 127.5 | 0 |
| 7(1, G1) | 14snap | 130.5 | 2 |
| 8(1, H1) | 14snap | 125.5 | 0.5 |
| 9(1, A2) | 12snap | 170 | 0 |
| 10(1, B2) | 12snap | 157.5 | 2.5 |
| 11(1, C2) | 12snap | 162.5 | 1 |
| 12(1, D2) | 12snap | 162 | 0.5 |
| 13(1, E2) | TIF | 34.5 | 5 |
| 14(1, F2) | TIF | 32 | 0 |
| 15(1, G2) | TIF | 36 | 0 |
| 16(1, H2) | TIF | 32 | 3 |

Figure 8:
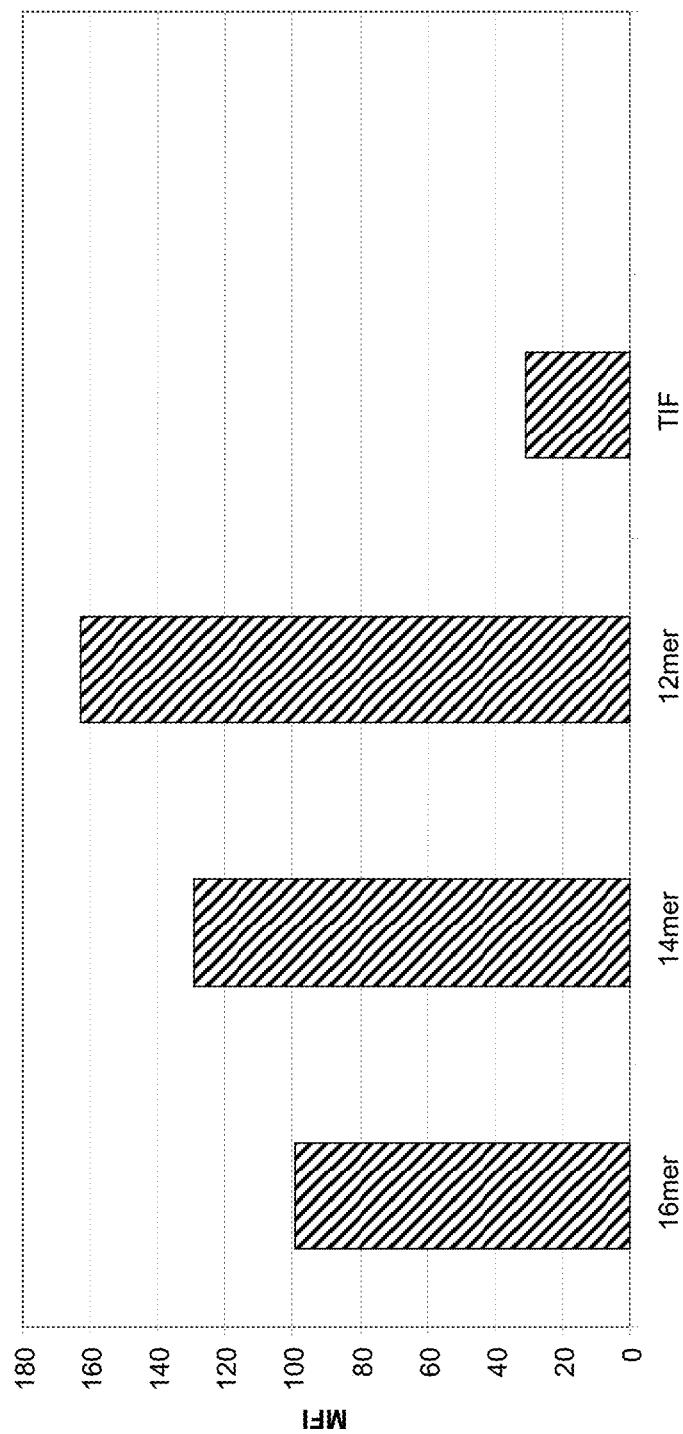
FIG. 8 is a graph showing a comparison of 12-, 14-, and 16-mer stem hairpin primers, and non-hairpin forming primers (TIF), in a PCR with aptaTaq exo(−) polymerase.

The data from Table 11 is also represented graphically in FIG. 8. All of the hairpin-forming primers (16snap, 14snap, and 12snap) significantly outperformed the non-hairpin-forming primer (TIF).

F. Example 6

The PCR cocktail as described above in the apta taq PCR was used as a hybridization buffer for hybridizing a labeled oligo complimentary to the primer region for each of the 16snap, 14snap, 12snap, and TIF primers. As shown in Table 12, the hairpin structure of the 16snap, 14snap, and 12snap primers largely inhibited their ability to hybridize to the beads.

TABLE 12

| Location | Sample | Analyte 27 MFI | Analyte 33 MFI |
|---|---|---|---|
| 1(1, A1) | 16snap | 12.5 | 9 |
| 2(1, B1) | 16snap | 10.5 | 8 |
| 3(1, C1) | 14snap | 16 | 12 |
| 4(1, D1) | 14snap | 19 | 9 |
| 5(1, E1) | 12snap | 35 | 10.5 |
| 6(1, F1) | 12snap | 35 | 9.5 |
| 7(1, A2) | TIF | 425 | 12 |
| 8(1, B2) | TIF | 427 | 13.5 |

G. Example 7

Oligos were also made for the amplification of the prothrombin gene. These oligos were as follows:

```
PT TIF:
                                       (SEQ ID NO: 10)
CAA TTC AAA TCA CAA TAA TCA ATC /iSp18/CTT CCT GAG

CCC AGA GAG C

12SNAP/ptu:
                                       (SEQ ID NO: 11)
CAA TTC AAA TCA CAA TAA TCA ATC /iSp18/ACA CTC CAC

ACATGA TTT GAA TTG CTT CCT GAG CCC AGA GAG C

PtdCY3:
                                       (SEQ ID NO: 12)
/5Cy3/ GTC ATT GAT CAG TTT GGA GAG TAG G

BeadPT:
                                       (SEQ ID NO: 13)
/5AmMC12/GAT TGA TTA TTG TGA TTT GAA TTG FVmutant oligo FV506Q2:
                                       (SEQ ID NO: 14)
/5AmMC12/GTATTCCTTGCCTGTCCA
```

The BeadPT oligo was coupled to bead set 29. The Analyte 33 and Analyte 27 bead sets from the MTHFR studies described above, were used as negative controls.

Two PCR cocktails were prepared sharing all the same reagents with the exception of the forward primers (PT TIF and 12SNAP/ptu). A no template control was added as well as 3 template added samples for each condition. The PCR cocktail is shown in Table 13. Results are shown in Table 14.

TABLE 13

| | |
|---|---|
| 10x ThermoPol Buffer | 5 μl |
| H$_2$O | 34.7 μl |
| Primer | 2 μl (400 nM) |
| Template #24 | 0.3 μl (100 ng) |
| Beads | 2 μl (5,000 beads) |
| dNTPs | 1 μl (0.2 mM) |
| Deep Vent Polymerase (New England BioLabs) | 2 μl (10 Units) |
| MgSO$_4$ | 3 μl (8 mM) |
| Total | 50 μl |

TABLE 14

| Location | Sample | Analyte 27 MFI | Analyte 29 MFI | Analyte 33 | Total Events |
|---|---|---|---|---|---|
| 1(1, A1) | 12SNAP/ptu, no template | 14.5 | 10 | 23 | 184 |
| 2(1, B1) | 12SNAP/ptu | 10.5 | 78 | 12.5 | 415 |
| 3(1, C1) | 12SNAP/ptu | 6.5 | 84 | 14 | 322 |
| 4(1, D1) | PT TIF, | 7 | 16 | 17 | 346 |
| 5(1, E1) | PT TIF | 15 | 38 | 14 | 336 |
| 6(1, F1) | PT TIF | 6 | 36.5 | 10.5 | 193 |

From the results in Table 14, it can be seen that the signal difference of the 12SNAP/ptu primer is about double that of the PT TIF primer after 27 cycles using 400 nM primer concentrations with a PCR protocol of: 97° C., 5 minutes; (97° C., 30 seconds; 55° C., 30 seconds; 72° C., 30 seconds)×27 cycles; followed by 7 minutes at 72° C. These results also demonstrated that the PT primers will not cross hybridize with the MHFTR primer sets if combined into a multiplex reaction.

H. Example 8

A pseudo real-time PCR was performed in which a PCR cocktail (with DeepVent exo (-) polymerase) was divided into 16 aliquots for each primer set. Each aliquot was removed from the thermal cycler at progressive cycles to measure the signal levels at each cycle. This was done using a fast 2-step PCR reaction, and aliquots were measured on an LX200 (Luminex) at room temperature at the end of the PCR protocol of 36 cycles total.

Figure 9:
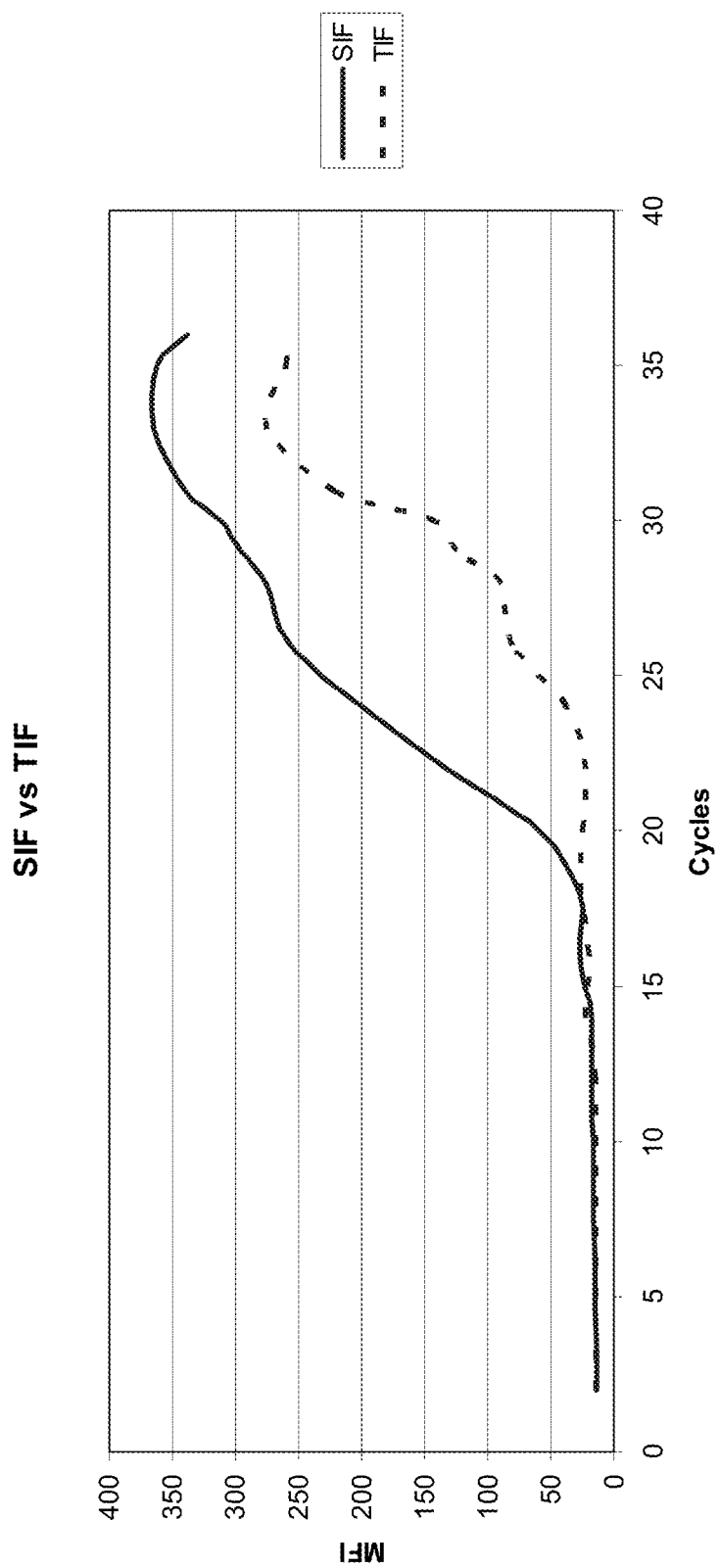
FIG. 9 is a graph of the MFI at various PCR cycles in a pseudo real-time PCR with either a hairpin-forming forward primer or a non-hairpin forming forward primer.

As shown in FIG. 9 signal was observable at just 22 cycles (44 minutes) for the 12SNAP/ptu primer compared to 29 cycles (58 min.) for the PT TIF primer. In addition to producing an observable signal earlier, it can be seen in FIG. 9 that the hairpin forming primer also was more sensitive. At cycle 22 the PT TIF primer was only 16% of the signal compared to the 12SNAP/ptu primer, and only 75% at peak cycle 33.

I. Example 9

A real-time PCR experiment was performed on a glass slide with the lens and hex-illuminator directly over the slide for the duration of the experiment. Glass slide chambers were constructed, and the glass was chemically modified using DMDCS followed by a dip in Polyadenylic Acid Potassium salt. A glass slide and a cover slip were joined together with a sticky gasket (BioRad) using an in situ PCR kit. These were placed onto a BioRad DNA Engine thermal cycler equipped with a slide griddle. This particular slide griddle had a hole drilled in it, directly over one of the 96 wells. The exposed well was painted black. The glass chamber was placed directly over the hole in the griddle to reduce background reflection light. A real-time PCR unit was constructed by coupling a CCD camera and light source to the DNA Engine thermal cycler. The Hex-illuminator was placed directly over the glass slide and remained there for the duration of the PCR reaction. The following cocktail was placed in the 25 μL volume glass chamber:

TABLE 15

| | |
|---|---|
| 10x ThermoPol Buffer | 5 μl |
| H$_2$O | 34.7 μl |
| Primer 12SNAP/ptu & PtdCY3 | 200 nM each |
| Template #24 | 0.3 μl (100 ng) |
| Beads | 2 μl (5,000 beads) |
| dNTPs | 1 μl (0.2 mM each) |
| Deep Vent Polymerase (New England BioLabs) | 2 μl (10 Units) |
| MgSO$_4$ | 3 μl (8 mM) |
| Total | 50 μl |

The following PCR Cycling conditions were run: 1) 97° C. for 5 min; 2) 105° C. for 15 s; 3) 96° C. for 30 s; 4) 50° C. for 5 s; 5) 68° C. for 30 s; 6) Go to 2, 5 times; 7) 15° C. for 10 s; 8) 24° C. for 5 min; 9) Go to 2, 6 times; 10) End. These conditions included extra ramp times to account for the heating delay of the griddle.

Figure 10:
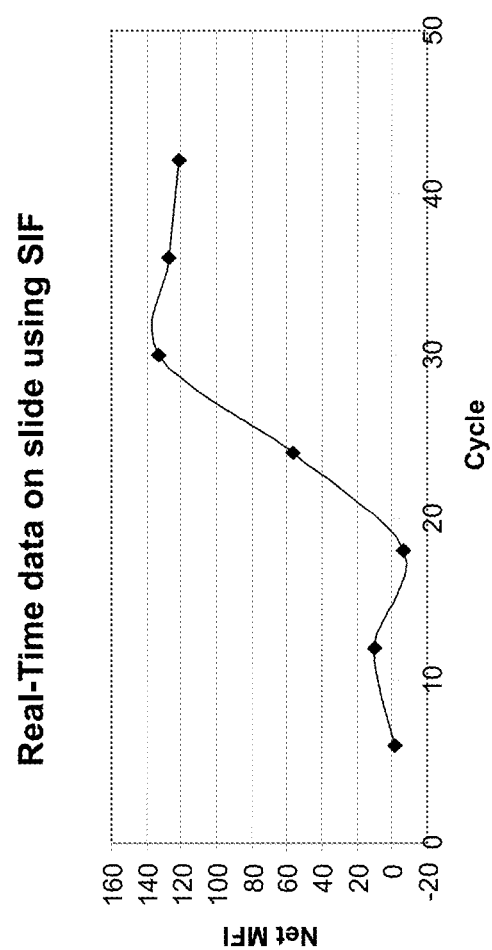
FIG. 10 is a graph of the MFI at various PCR cycles in a real-time PCR.

Images of the beads were taken at exactly 4 minutes at each 5 cycle interval at 24° C. The glass chamber was not agitated in between runs. The data are shown in Table 16 and FIG. 10.

TABLE 16

| Cycle before | Bead | MFI |
| --- | --- | --- |
| 6 | 1 | 251 |
|  | 2 | 232 |
| 12 | 1 | 246 |
|  | 2 | 248 |
| 18 | 1 | 235 |
|  | 2 | 241 |
| 24 | 1 | 276 |
|  | 2 | 220 |
| 30 | 1 | 316 |
|  | 2 | 183 |
| 36 | 1 | 281 |
|  | 2 | 154 |
| 42 | 1 | 299 |
|  | 2 | 178 |

J. Example 10

Optimization of the length of the stem region of the hairpin used in the primer that contains the universal Tag sequence that binds to the universal labeled probe upon extension of the opposite strand was evaluated. In order to find the optimal length of the reverse primer hairpin stem region length, and the length of the universal reporter probes, a series of primers with different stem lengths and universal reporter probes with different lengths were reacted for comparison.

In these reactions reverse hairpin primers with 11mer, 14mer, 16mer and 0 mer stem lengths were used. These were hybridized with beads that were coupled to probes that were complimentary to the target specific primer regions of each of these hairpin primers. Each 50 uL reaction contained:

- 8 mM MgCl$_2$
- 1× Qiagen PCR buffer
- 5000 beads
- 200 nM of primer
- 200 nM of universal reporter probe All reagents were hybridized at 95° C. for 5 min. followed by 37° C. for 15 minutes. The Luminex magnetic beads were then analyzed on a Luminex Lx200 analyzer.

The following oligos were used in this reaction:

```
BeadTagantiprime
                                         (SEQ ID NO: 15)
/5AmMC12/TAG TTG CAA ATC CGC GAC AA NoSnaprevNei
                                         (SEQ ID NO: 16)
ATG ATG ATG TAT TGT AGT TAT GAA /iSp18/AGG TAT TGA

AGT TTT GTC GCG GAT TTG CAA CTA

Univlabeled13
                                         (SEQ ID NO: 17)
/5Cy3/AAT ACA TCA TCA T/3InvdT/

UnivLabeled 15
                                         (SEQ ID NO: 18)
/5Cy3/ACA ATA CAT CAT CAT /3InvdT/

Snap11revNei
                                         (SEQ ID NO: 19)
ATG ATG ATG TAT TGT AGT TAT GAA /iSp18/TAC ATC ATC

ATT TGT CGC GGA TTT GCA ACT A

Snap14RevNei
                                         (SEQ ID NO: 20)
ATG ATG ATG TAT TGT AGT TAT GAA /iSp18/CAA TAC ATC

ATC ATT TGT CGC GGA TTT GCA ACT A

Snap16RevNei
                                         (SEQ ID NO: 21)
ATG ATG ATG TAT TGT AGT TAT GAA /iSp18/TAC AAT ACA

TCA TCA TTT GTC GCG GAT TTG CAA CTA
```

TABLE 17

| Rev primer type | universal probe | MFI |
| --- | --- | --- |
| Snap11revNei | Univlabeled13 | 8 |
| Snap11revNei | Univlabeled13 | 6 |
| Snap11revNei | UnivLabeled 15 | 40 |
| Snap11revNei | UnivLabeled 15 | 43 |
| Snap14RevNei | Univlabeled13 | 3 |
| Snap14RevNei | Univlabeled13 | 3 |
| Snap14RevNei | UnivLabeled 15 | 3 |
| Snap14RevNei | UnivLabeled 15 | 4 |
| Snap16RevNei | Univlabeled13 | 3 |
| Snap16RevNei | Univlabeled13 | 1 |
| Snap16RevNei | UnivLabeled 15 | 2 |
| Snap16RevNei | UnivLabeled 15 | 2 |
| NoSnaprevNei | Univlabeled13 | 929 |
| NoSnaprevNei | Univlabeled13 | 1009 |
| NoSnaprevNei | UnivLabeled 15 | 862 |
| NoSnaprevNei | UnivLabeled 15 | 1399 |

The goal of this study was to find a primer/probe pair such that the hairpin region of the primer would remain in the closed state in the presence of the universal labeled probe, but remain in the open state once a double stranded amplicon product was formed in the presence of the universal labeled probe. In order to ensure that the hairpin would remain in the open state after formation of the double stranded product, we chose a primer/probe pair such that the hairpin monomer was of a strong enough binding energy so as to remain in the closed state, but of a weak enough binding energy so as to remain in the open state in the presence of the double stranded product and universal labeled probe. Such a pair would have to near the point of open state in this study. The best pair was identified as the Snap11revNei/Univlabeled13 pair. This pair was chosen to be used in subsequent PCR reactions because the low MFI indicates that it is in the closed state, but if a longer universal labeled probe is used, some of the hairpins open, as indicated by the 40-43 MFIs. This indicates that the Snap11revNei/Univlabeled13 is closed, but it is near the point at which some would be open.

K. Example 11

A dilution series of *Neiseria Meningitidis* DNA (ATCC 700532D-5) in a real-time quantitative PCR was performed in a closed tube. This experiment demonstrated the ability to perform quantitative real-time PCR in order to discriminate between varying input concentrations of template DNA. A PCR cocktail was prepared such that each 25 uL reaction contained:

- 8 mM MgCl$_2$
- 1× Qiagen PCR buffer
- 5000 beads of each region
- 200 nM of primer
- 200 nM of universal reporter probe A sample of *Neiseria Meningitidis* DNA was amplified in real-time using sealed glass chambers and placed on a thermal cycler fitted with a slide griddle. These reactions were performed as in Example 11. The first sealed chamber contained 1 million copies of DNA, the second chamber contained 100,000 copies, and the third chamber contained 10,000 copies of N. Meningitidis DNA.

Two bead sets were used in this experiment. One bead set (Set 2) was coupled to a probe (BeadTag Nei) that was complimentary to the tag region of the forward primer (Snap12fwdShrtNei). The other bead set (Set 1) was coupled to a probe (BeadTag antiList) that was not specific to hybridize to anything in the reaction. Set 1 was used to monitor the non-specific signal in the reaction and to act as a normalization and background subtract tool to account for differences in light intensity for each image taken.

```
Snap11revNei
                                        (SEQ ID NO: 22)
ATG ATG ATG TAT TGT AGT TAT GAA /iSp18/TAC ATC ATC

ATT TGT CGC GGA TTT GCA ACT A

BeadTag Nei
                                        (SEQ ID NO: 23)
/5AmMC12/GAT TGA TAT TTG AAT GTT TGT TTG /3InvdT/

Snap12fwdShrtNei
                                        (SEQ ID NO: 24)
CAA ACA AAC ATT CAA ATA TCA ATC /iSp18/AAT GTT TGT

TTG GCT GCG GTA GGT GGT TCA A

Univlabeled13
                                        (SEQ ID NO: 25)
AAT ACA TCA TCA T/3Cy3/

BeadTag antiList
                                        (SEQ ID NO: 26)
/5AmMC12/GTT TGT ATT TAG ATG AAT AGA AAG /3InvdT/
```

The data for each bead set for each cycle is given below. The average MFI for each bead Set 1 for each time point in all 3 reactions was 3931 MFI. This average value was used to create a normalization factor by dividing the non-specific bead set (Set 1) by 3931 MFI. Each raw data point was divided by this normalization factor that was specific to each time point. After normalization, the specific bead set for detecting Neiseria Meningitidis (Set 2) normalized MFI was subtracted by Set 1 normalized MFI. This calculation resulted in a net normalized MFI for Set 2 for each time point. The data are given in the table below.

TABLE 18

| Cycle | Bead Set | Raw Median | Normalization Factor | Net MFI | Normalized MFI | Net Normalized MFI |
|---|---|---|---|---|---|---|
| 1 million copies ||||||| 
| 0 | 1 | 3757 | 0.96 | 127 | 3931 | 133 |
|   | 2 | 3884 |      |     | 4064 |     |
| 12 | 1 | 3120 | 0.79 | -76 | 3931 | -96 |
|    | 2 | 3044 |      |     | 3836 |     |
| 18 | 1 | 3124 | 0.79 | 158 | 3931 | 199 |
|    | 2 | 3282 |      |     | 4130 |     |
| 24 | 1 | 3009 | 0.77 | 563 | 3931 | 736 |
|    | 2 | 3572 |      |     | 4667 |     |
| 30 | 1 | 2863 | 0.73 | 601 | 3931 | 825 |
|    | 2 | 3464 |      |     | 4757 |     |
| 100,000 copies |||||||
| 0 | 1 | 3931 | 1.00 | -15 | 3931 | -15 |
|   | 2 | 3916 |      |     | 3916 |     |
| 6 | 1 | 4120 | 1.05 | 18 | 3931 | 17 |
|   | 2 | 4138 |      |    | 3949 |    |
| 12 | 1 | 4403 | 1.12 | 58 | 3931 | 52 |
|    | 2 | 4461 |      |    | 3983 |    |

TABLE 18-continued

| Cycle | Bead Set | Raw Median | Normalization Factor | Net MFI | Normalized MFI | Net Normalized MFI |
|---|---|---|---|---|---|---|
| 18 | 1 | 4431 | 1.13 | 154 | 3931 | 137 |
|    | 2 | 4585 |      |     | 4068 |     |
| 24 | 1 | 4396 | 1.12 | 579 | 3931 | 518 |
|    | 2 | 4975 |      |     | 4449 |     |
| 30 | 1 | 4083 | 1.04 | 790 | 3931 | 761 |
|    | 2 | 4873 |      |     | 4692 |     |
| 36 | 1 | 4175 | 1.06 | 787 | 3931 | 741 |
|    | 2 | 4962 |      |     | 4673 |     |
| 10,000 copies |||||||
| 0 | 1 | 4220 | 1.07 | 136 | 3931 | 127 |
|   | 2 | 4356 |      |     | 4058 |     |
| 6 | 1 | 4417 | 1.12 | 244 | 3931 | 217 |
|   | 2 | 4661 |      |     | 4149 |     |
| 12 | 1 | 4819 | 1.23 | 210 | 3931 | 171 |
|    | 2 | 5029 |      |     | 4103 |     |
| 18 | 1 | 4671 | 1.19 | 144 | 3931 | 121 |
|    | 2 | 4815 |      |     | 4053 |     |
| 24 | 1 | 4671 | 1.19 | 144 | 3931 | 121 |
|    | 2 | 4815 |      |     | 4053 |     |
| 30 | 1 | 3326 | 0.85 | 521 | 3931 | 616 |
|    | 2 | 3847 |      |     | 4547 |     |
| 36 | 1 | 3162 | 0.80 | 699 | 3931 | 869 |
|    | 2 | 3861 |      |     | 4801 |     |

Figure 11:
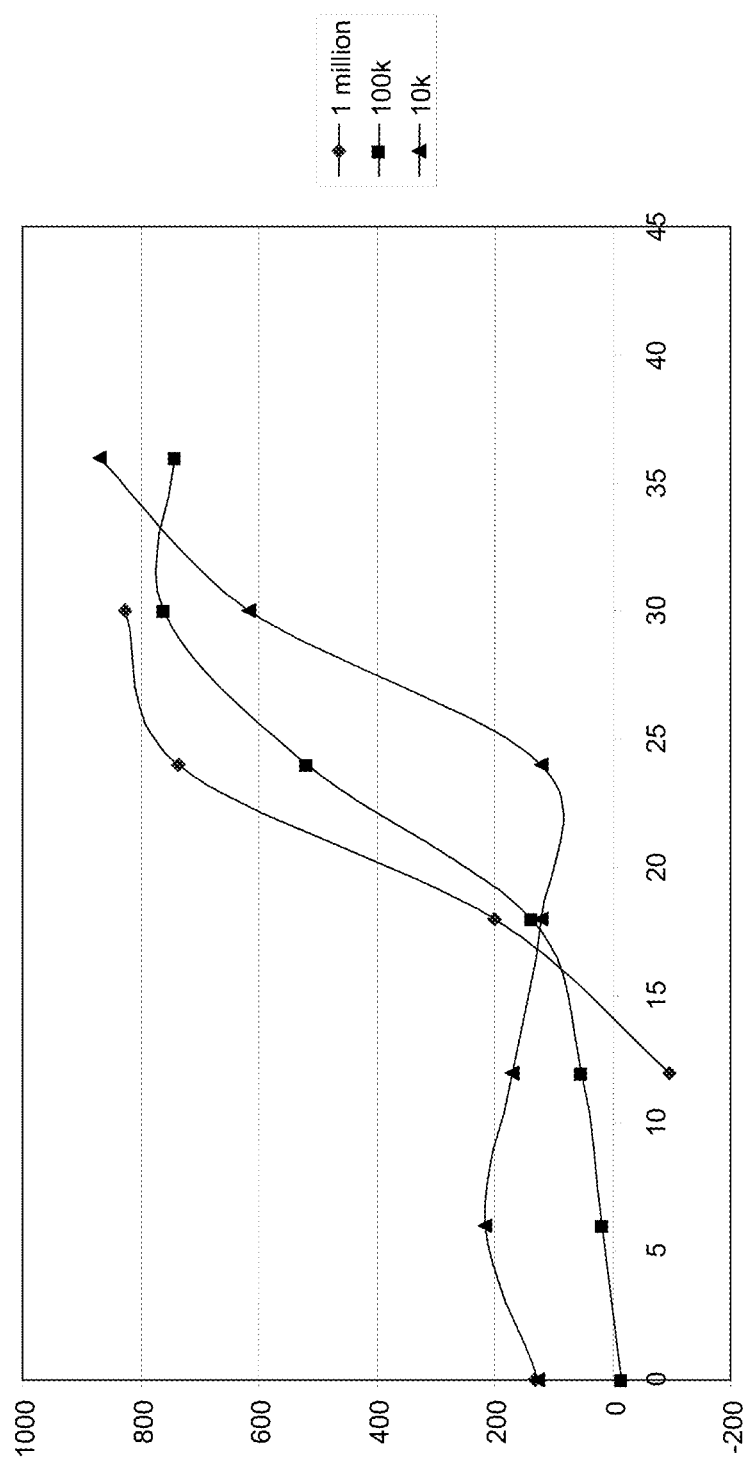
FIG. 11 is a graph representing a dilution series of *Neiseria Meningitidis* DNA in a real-time quantitative PCR.
Figure 12:
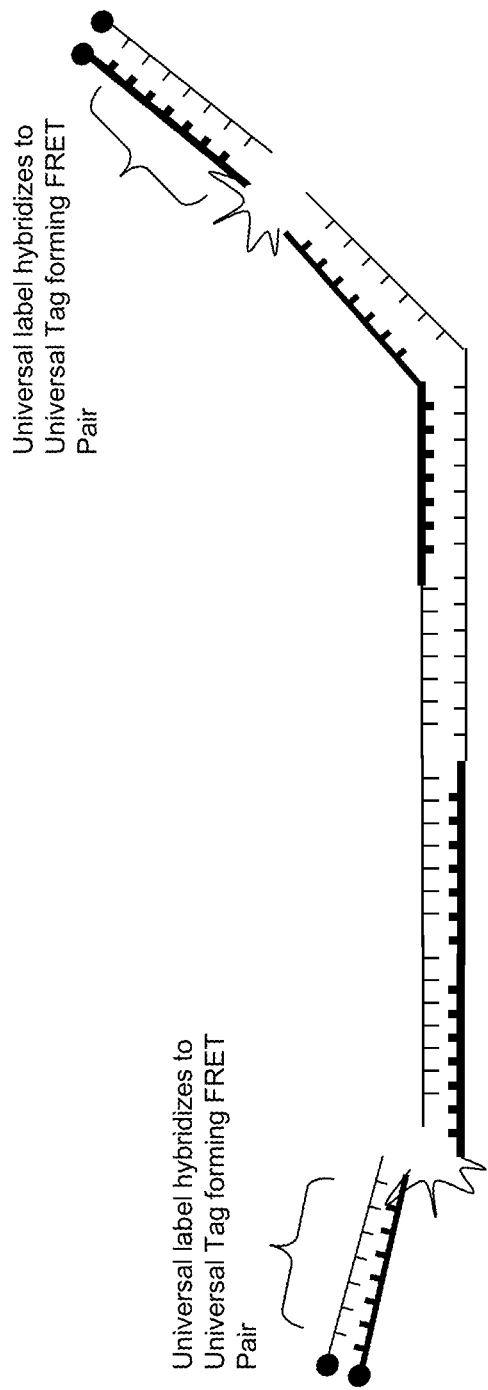
FIG. 12 illustrates a real-time PCR assay chemistry. Upon extension of the primers the hairpin portions open up allowing binding to a labeled probe, such that Forster Resonance Energy Transfer (FRET) occurs allowing real-time detection in standard real-time thermal cyclers. An advantage of this chemistry is that the end-users need only design the primers, once they are provided with the validated hairpin sequence, making it very design friendly. No beads are required in this assay.
Figure 13:
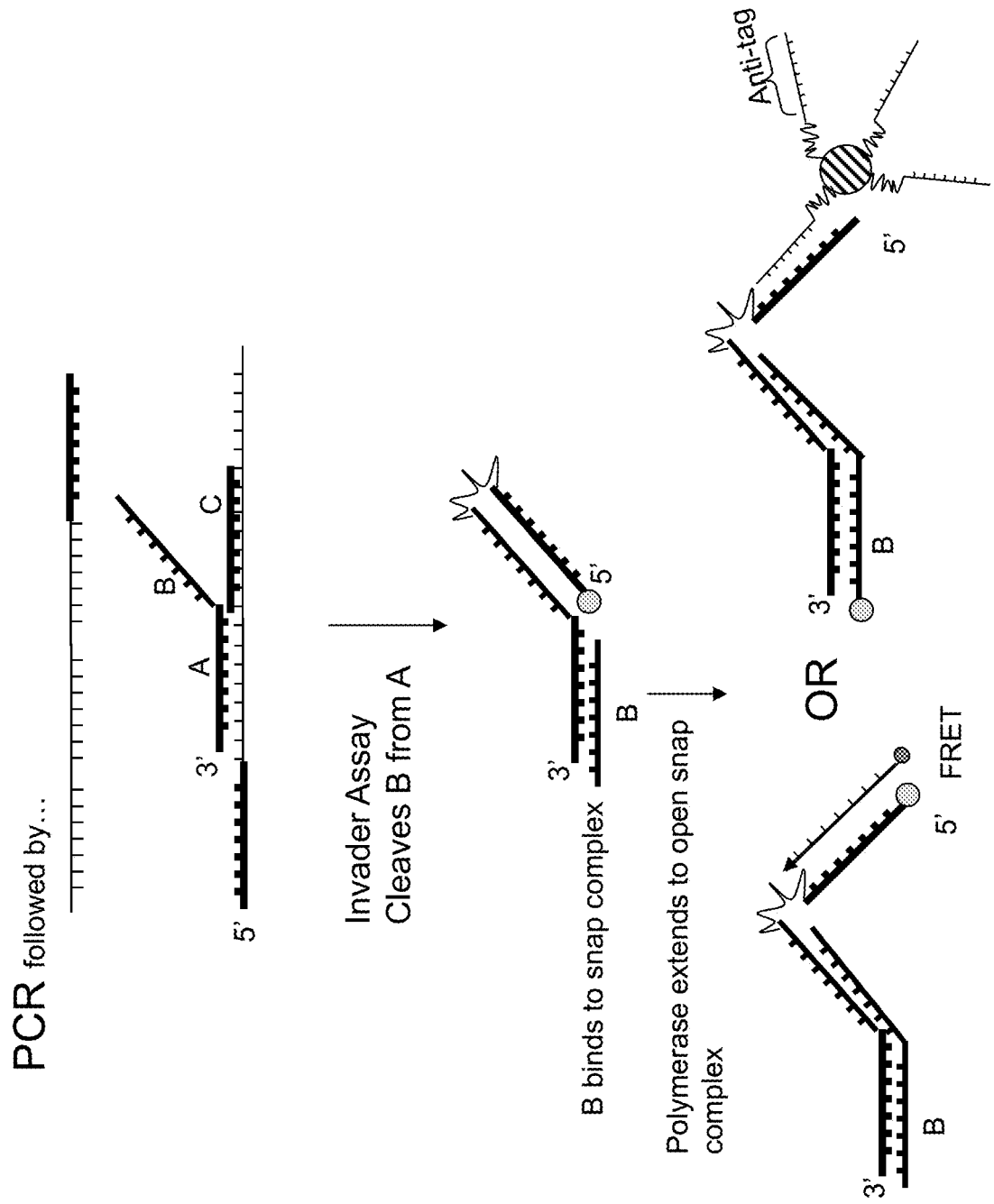
FIG. 13 illustrates an assay format in which hairpin-forming probes are used with an Invader assay. In the Invader assay the flap portion of the probe (B) is cleaved. Flap portion (B) can then act as a primer that can open up the hairpin sequence by polymerase extension. With the tag region of the hairpin sequence now available for binding it may bind to a labeled probe in a FRET pair for beadless real-time detection or it may bind to a bead for high multiplex detection.
Figure 14:
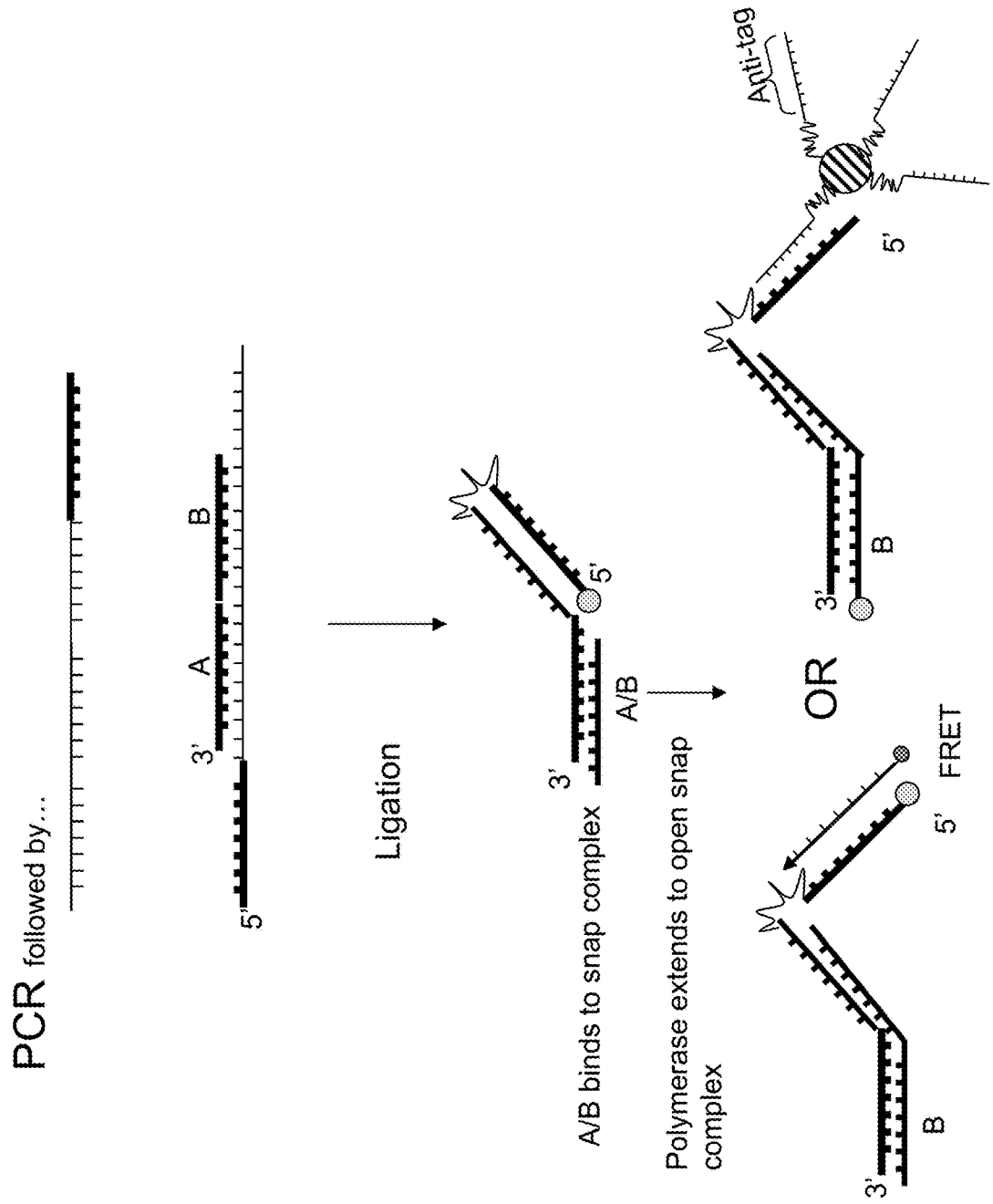
FIG. 14 illustrates an assay that incorporates the use of a ligation mechanism, such that the assay is held at a high enough temperature so that probes A and B cannot hybridize to the hairpin primer/probe unless they are ligated. Once they are ligated, they are of sufficient binding strength to bind to the probe/primer and extend in the presence of a strand displacement polymerase. With the tag region of the hairpin sequence now available for binding it may bind to a labeled probe in a FRET pair for beadless real-time detection or it may bind to a bead for high multiplex detection.
Figure 15:
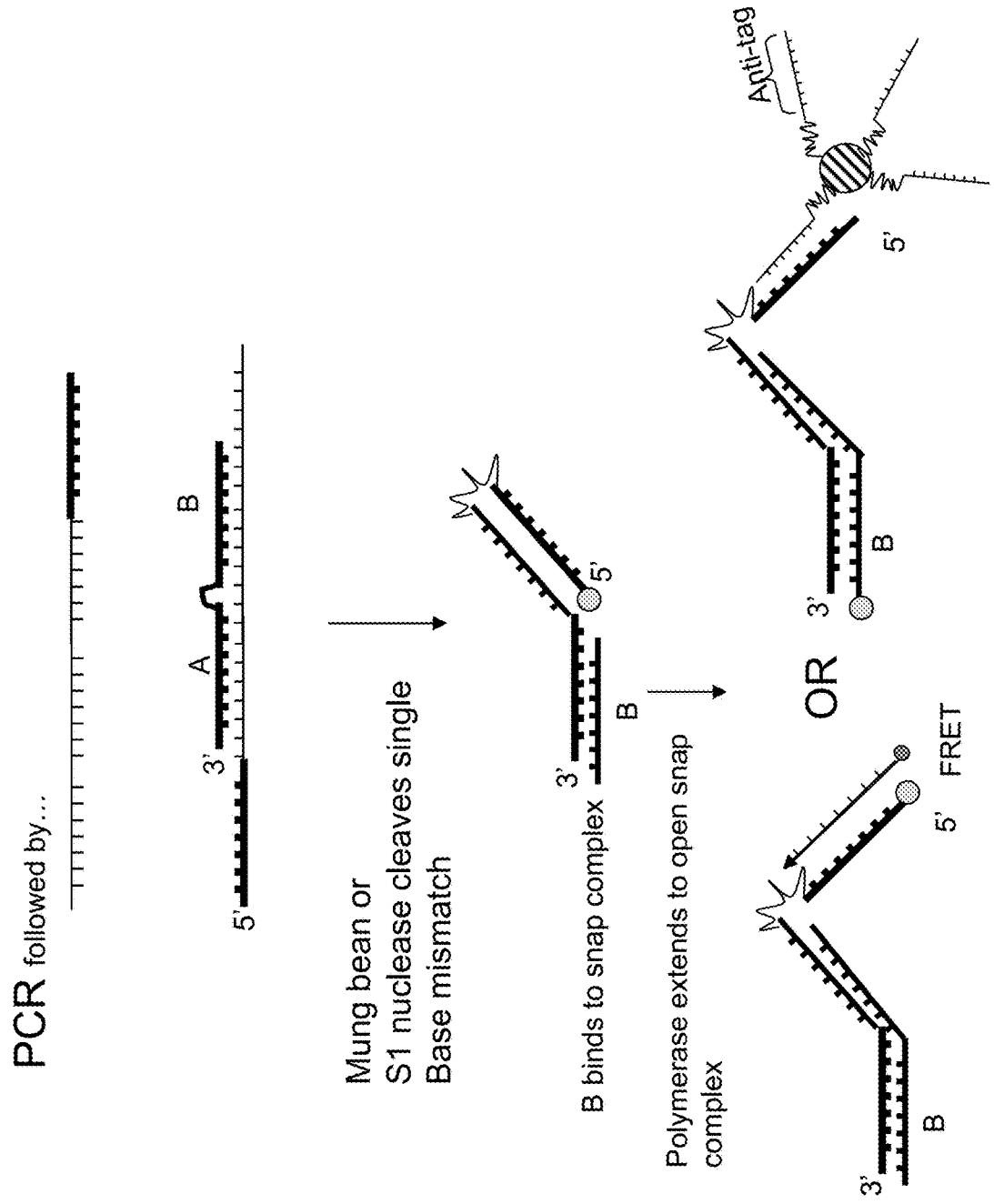
FIG. 15 illustrates an assay that incorporates the use of a mung bean or Si nuclease, which has the ability to cleave single base mismatches. Once the mismatch is cleaved, B can now act as a primer that can displace the hairpin, allowing the tag to be exposed for binding to a probe, which may or may not be attached to a solid surface.

A graph of this data (FIG. 11) shows a clear distinction between each of the input concentrations of N. Meningitidis which allows for quantitation.

L. Example 12

The following results demonstrate the ability to multiplex hairpin-forming primers for the detection of pathogens. A 3-plex meningitis assay was designed to detect Neisseria Meningitidis, Listeria Monocytogenes, and Haemophilus Influenzae. Three primer sets were multiplexed in the same reaction. Genomic DNA from separate bacteria species were placed in individual reactions to demonstrate the specificity of the assay.

The following primer and probe sequences were ordered from IDT and used.

```
Primer Set 1:
SIF4fwdList-t88
                                        (SEQ ID NO: 27)
TTA CTT CAC TTT CTA TTT ACA ATC /iSp18/AAG TGA AGT

AAA TTG CGA AAT TTG GTA CAG C

SIF13RCrevList
                                        (SEQ ID NO: 28)
ATG ATG ATG TAT TGT AGT TAT GAA /iSp18/TAC ATC ATC

ATC TGA TTG CGC CGA AGT TTA CAT TC

Primer Set 2:
SIFprobeFwdHaem-t86
                                        (SEQ ID NO: 29)
CTA ATT ACT AAC ATC ACT AAC AAT /iSp18/GTT AGT AAT

TAG TTG TTT ATA ACA ACG AAG GGA CTA ACG T

SIFrevHaem
                                        (SEQ ID NO: 30)
ATG ATG ATG TAT TGT AGT TAT GAA /iSp18/TAC ATC ATC

ATG ATT GCG TAA TGC ACC GTG TT
```

-continued

Primer Set 3:
Snap12fwdShrtNei (SEQ ID NO: 31)
CAA ACA AAC ATT CAA ATA TCA ATC /iSp18/AAT GTT TGT

TTG GCT GCG GTA GGT GGT TCA A

Snap11revNei (SEQ ID NO: 32)
ATG ATG ATG TAT TGT AGT TAT GAA /iSp18/TAC ATC ATC

ATT TGT CGC GGA TTT GCA ACT A

Probes coupled to Beads:
Bead Set 27/Specific for N. meningitidis fwd.
primer:

(SEQ ID NO: 33)
/5AmMC12/GAT TGA TAT TTG AAT GTT TGT TTG /3InvdT/

Bead Set 62/Specific for L. Monocytogenes fwd.
primer:

(SEQ ID NO: 34)
GAT TGT AAA TAG AAA GTG AAG TAA /3AmM/

Bead Set 67/Specific for H. Influenzae fwd.
primer:

(SEQ ID NO: 35)
ATT GTT AGT GAT GTT AGT AAT TAG /3AmM/

Universal Labeled Probe: 13Uni- (SEQ ID NO: 36)
AAT ACA TCA TCA T/3Cy3Sp/

The following volumes in μL were used in each PCR cocktail:

TABLE 19

| Material | 1x volume |
|---|---|
| 10x Buffer | 5 |
| H20 | 35.1 |
| Primer set 1 (10 μM) | 1 |
| Primer set 2 (10 μM) | 1 |
| Primer set 3 (10 μM) | 1 |
| Each Template | 1 |
| dntps (10 mM) | 1 |
| Polymerase (50 U/μL) | 0.2 |
| MgCl2 (50 mM) | 6 |
| Bead Set 1 (5000 beads/μL) | 0.5 |
| Bead Set 2 (5000 beads/μL) | 0.5 |
| Bead Set 3 (5000 beads/μL) | 0.5 |
| U13 (100 μM) | 0.2 |
| TOTAL | 53 |

PCR Materials: (Roche) Apta Taq delta exo DNA pol., Glycerol free, 50U/ul—Sample 2, 5KU(100 ul); (Roche PN:13409500) PCR Buffer without MgCl2, 10× concentration; (Invitrogen PN:18427-088) 10 mM dNTP Mix.

Thermal Cycling Parameters: 97° C. for 4 min; then 35 cycles of: (97° C. for 30 sec, 62° C. for 30 sec); then 72° C. for 7 min.

Each bead set was previously prepared using Luminex MagPlex-C Magnetic Microspheres by coupling their respective probe sequences using Luminex recommended EDC coupling procedures.

The following genomic DNA samples were obtained from American Type Culture Collection (ATCC):

TABLE 20

| Item Number | Description | Lot Number |
|---|---|---|
| 700532D-5 DR | *Neisseria meningitidis*; Strain FAM18 | 7385221 |
| BAA-679D-5 DR | *Listeria monocytogenes*; Strain EGDe | 57878064 |
| 51907D FZ | *Haemophilus influenzae* | 2662083 |

After the PCR reaction, samples were heated to 95° C. for 2 minutes and placed at room temperature for 8 minutes prior to analyzing on a Luminex 200 analyzer. 100 bead events per bead set were collected and a Median Fluorescence Intensity (MFI) value was derived for each bead set in each reaction. The following MFI values were obtained for each sample:

TABLE 21

| Input Genomic DNA | Bead Set 27 | Bead Set 62 | Bead Set 67 |
|---|---|---|---|
| Sample 1 *H. Influenza* | 7 | 10 | 67 |
| Sample 2 *L. Monocytogenes* | 6 | 87 | 3 |
| Sample 3 *N. Meningitidis* | 73 | 13.5 | 0 |
| Sample 4 No Template | 2 | 9.5 | 0 |

These results demonstrate the multiplex ability of hairpin primers.

The portions of the primer sets that are target specific to the different bacterial species were obtained from the following publicly available references:

*Neisseria Meningitidis:*

Corless, C. E., Guiver, M., Borrow, R., Edwards-Jones, V., Fox, A. J., and Kaczmarski, E. 2001. Simultaneous Detection of *Neisseria Meningitidis, Haemophilus Influenzae*, and *Streptococcus Pneumoniae* in Suspected Cases of Meningitis and Septicemia Using Real-Time PCR. Journal of Clinical Microbiology. 39: 1553-1558.

*Listeria monocytogenes:*

Johnson, w., Tyler, S., Ewan, E., Ashton, F., Wang, G. and Rozee, K. 1992. Detection of Genes Coding for Listeriolysin and *Listeria monocytogenes* Antigen A (LmaA) in *Listeria* spp. by the Polymerase Chain Reaction. Microbial Pathogenesis 12; 79-86.

Bohnert, M., Dilasser, F., Dalet, C. Mengaud, J. and Cossart, P. 1992. Use of Specific Oligonucleotides for Direct Enumeration of *Listeria monocytogenes* in Food Samples by Colony Hybridization and Rapid Detection by PCR. Res. Microbiol. 143; 271-280.

*Haemophilus Influenzae:*

Maaroufi, Y., Bruyne, J., Heymans, C., and Crokaert, F. 2007. Real-Time PCR for Determining Capsular Serotypes of *Haemophilus Influenzae*. Journal of Clinical Microbiology. 45: 2305-2308.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,284,412
U.S. Pat. No. 4,498,766
U.S. Pat. No. 4,659,774
U.S. Pat. No. 4,661,913
U.S. Pat. No. 4,682,195
U.S. Pat. No. 4,683,202
U.S. Pat. No. 4,714,682
U.S. Pat. No. 4,767,206
U.S. Pat. No. 4,774,189
U.S. Pat. No. 4,816,571
U.S. Pat. No. 4,857,451
U.S. Pat. No. 4,883,750
U.S. Pat. No. 4,942,124
U.S. Pat. No. 4,959,463
U.S. Pat. No. 4,989,977
U.S. Pat. No. 5,137,806
U.S. Pat. No. 5,141,813
U.S. Pat. No. 5,160,974
U.S. Pat. No. 5,264,566
U.S. Pat. No. 5,428,148
U.S. Pat. No. 5,478,722
U.S. Pat. No. 5,525,494
U.S. Pat. No. 5,539,082
U.S. Pat. No. 5,554,744
U.S. Pat. No. 5,574,146
U.S. Pat. No. 5,595,890
U.S. Pat. No. 5,602,244
U.S. Pat. No. 5,639,611
U.S. Pat. No. 5,645,897
U.S. Pat. No. 5,654,413
U.S. Pat. No. 5,705,629
U.S. Pat. No. 5,714,331
U.S. Pat. No. 5,719,262
U.S. Pat. No. 5,736,330
U.S. Pat. No. 5,736,336
U.S. Pat. No. 5,766,855
U.S. Pat. No. 5,773,571
U.S. Pat. No. 5,786,461
U.S. Pat. No. 5,837,832
U.S. Pat. No. 5,837,860
U.S. Pat. No. 5,840,873
U.S. Pat. No. 5,843,640
U.S. Pat. No. 5,843,650
U.S. Pat. No. 5,843,651
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,487
U.S. Pat. No. 5,849,497
U.S. Pat. No. 5,849,546
U.S. Pat. No. 5,849,547
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,882,864
U.S. Pat. No. 5,891,625
U.S. Pat. No. 5,905,024
U.S. Pat. No. 5,908,845
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,630
U.S. Pat. No. 5,922,574
U.S. Pat. No. 5,925,517
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 5,981,180
U.S. Pat. No. 6,057,107
U.S. Pat. No. 6,103,463
U.S. Pat. No. 6,287,778
U.S. Pat. No. 6,322,971
U.S. Pat. No. 7,226,737
U.S. Pat. No. 7,226,737
U.S. Pub. Appln. 2005/0191625
Egholm et al., *Nature*, 365(6446):566-568, 1993.
EP Appln. 266,032
EP Appln. 320,308
EP Appln. 329,822
Fodor et al., *Biochemistry*, 30(33):8102-8108, 1991.
Froehler et al., *Nucleic Acids Res.*, 14(13):5399-5407, 1986.
Frohman, In: *PCR Protocols: A Guide To Methods And Applications*, Academic Press, N.Y., 1990.
GB Appln. 2 202 328
Holmstrom et al., *Anal. Biochem.* 209:278-283, 1993.
Koshkin and Dunford, *J. Biol. Chem.*, 273(11):6046-6049, 1998a.
Koshkin and Wengel, *J. Org. Chem.*, 63(8):2778-2781, 1998b.
Kwoh et al., *Proc. Natl. Acad. Sci.* USA, 86:1173, 1989.
Mueller et al., *Current Protocols in Mol. Biol.*; 15:5,1993.
Newton et al., *Nucl. Acids Res.* 21:1155-1162, 1993.
Ohara et al., *Proc. Natl. Acad. Sci.* USA, 86:5673-5677, 1989.
PCT Appln. WO 00/47766
PCT Appln. WO 88/10315
PCT Appln. WO 89/06700
PCT Appln. WO 90/07641
PCT Appln. WO 92/20702
PCT Appln. WO 93/17126
PCT Appln. WO 9731256
PCT Appln. WO05087789

PCT Appln. WO07/085087
PCT Appln. PCT/EP/01219
PCT Appln. PCT/US87/00880
PCT Appln. PCT/US89/01025
Pease et al., *Proc. Natl. Acad. Sci.* USA, 91:5022-5026, 1994.

Rasmussen et al., *Anal. Biochem,* 198:138-142, 1991.
Running et al., *BioTechniques* 8:276-277, 1990.
Santalucia et al., *Biochemistry;* 38:3468-3477, 1999.
Wahlestedt et al., *Proc. Natl. Acad. Sci.* USA, 97(10):5633-5638, 2000.
Walker et al., *Nucleic Acids Res.* 20(7):1691-1696, 1992.

The invention claimed is:

1. A method for detecting a ligation product comprising a first oligonucleotide probe and a second oligonucleotide probe that are ligated together, the method comprising:
   (a) providing a third oligonucleotide probe comprising:
      (i) a ligation-product specific sequence, wherein the ligation-product specific sequence is complementary to at least a portion of both the first oligonucleotide probe and the second oligonucleotide probe of the ligation product;
      (ii) an anti-tag sequence 5' of the ligation-product specific sequence;
      (iii) a tag sequence 5' of the anti-tag sequence;
      (iv) a blocker between the anti-tag sequence and the tag sequence; and
      (v) a label;
   (b) hybridizing the third oligonucleotide probe to the ligation product at a temperature at which at least a portion of both the first oligonucleotide probe and the second oligonucleotide probe of the ligation product hybridizes to the third oligonucleotide probe but at which unligated subunits of the ligation product do not hybridize to the third oligonucleotide probe; and
   (c) detecting the hybridization of the oligonucleotide probe to the ligation product.

2. The method of claim 1, wherein the label is a Forster Resonance Energy Transfer (FRET) donor or acceptor molecule.

3. The method of claim 1, further comprising immobilizing the third oligonucleotide probe on a solid support.

4. The method of claim 3, wherein the third oligonucleotide probe is immobilized on a solid support by hybridization of the tag sequence to a complementary anti-tag sequence coupled to the solid support.

5. The method of claim 3, wherein the solid support is a bead.

6. A method for detecting a target nucleic acid, the method comprising:
   a) hybridizing first and second oligonucleotide probes to the target nucleic acid, wherein the first and second oligonucleotide probes are complementary to adjacent regions of the target nucleic acid:
   b) ligating hybridized first and second oligonucleotide probes to form a ligation product;
   c) denaturing the ligation product from the target nucleic acid;
   d) hybridizing the ligation product to a third oligonucleotide probe, the third oligonucleotide probe comprising, in a 3' to 5' direction, a hybridizing region that is complementary to at least a portion of the ligation product and a non-hybridizing region that is not complementary to the ligation product, wherein the third oligonucleotide hybridizes to at least a portion of both the first and second oligonucleotide probes;
   e) extending the ligation product along the third oligonucleotide probe to form an amplicon; and
   f) detecting the target nucleic acid by detecting the amplicon.

7. The method of claim 6, wherein the non-hybridizing region of the third oligonucleotide probe comprises:
   (i) an anti-tag sequence 5' of the hybridizing region that is complementary to at least a portion of the ligation product;
   (ii) a tag sequence 5' of the anti-tag sequence;
   (iii) a blocker between the anti-tag sequence and the tag sequence; and
   (iv) a label.

8. The method of claim 7 wherein the label is a FRET donor or a FRET acceptor molecule.

9. The method of claim 6 further comprising immobilizing the third oligonucleotide probe on a solid support.

10. The method of claim 7 wherein the third oligonucleotide probe is immobilized on a solid support by hybridizing the tag sequence to a complementary anti-tag sequence coupled to a solid support.

11. The method of claim 9 wherein the solid support is a bead.

12. The method of claim 8 further comprising hybridizing the tag sequence to a complementary FRET probe.

13. The method of claim 2 further comprising hybridizing the tag sequence to a complementary FRET probe.

* * * * *

SEQUENCE LISTING

```
<160> NUMBER OF SEQ ID NOS: 36

<210> SEQ ID NO 1
<211> LENGTH: 70
<212> TYPE: DNA
<213> ORGANISM: Artificial Sequence
<220> FEATURE:
<223> OTHER INFORMATION: Synthetic primer

<400> SEQUENCE: 1
caaacaaaca ttcaaatatc aatcctatct atacataatg tttgtttgca aggaggagct    60
gctgaagatg                                                           70

<210> SEQ ID NO 2
<211> LENGTH: 71
<212> TYPE: DNA
<213> ORGANISM: Artificial Sequence
<220> FEATURE:
<223> OTHER INFORMATION: Synthetic primer

<400> SEQUENCE: 2
caaacaaaca ttcaaatatc aatccctatc tatacataat gtttgtttgc aaggaggagc    60
tgctgaagat g                                                         71

<210> SEQ ID NO 3
<211> LENGTH: 69
<212> TYPE: DNA
<213> ORGANISM: Artificial Sequence
<220> FEATURE:
<223> OTHER INFORMATION: Synthetic primer

<400> SEQUENCE: 3
caaacaaaca ttcaaatatc aatcgattga tattgaatgt tgtttgcaa ggaggagctg     60 ctcaacatg                                                            69

<210> SEQ ID NO 4
<211> LENGTH: 70
<212> TYPE: DNA
<213> ORGANISM: Artificial Sequence
<220> FEATURE:
<223> OTHER INFORMATION: Synthetic primer

<400> SEQUENCE: 4
caaacaaaca ttcaaatatc aatcctatct atacatttac aaacattcca aggaggagct    60
gctgaagatg                                                           70

<210> SEQ ID NO 5
<211> LENGTH: 46
<212> TYPE: DNA
<213> ORGANISM: Artificial Sequence
<220> FEATURE:
<223> OTHER INFORMATION: Synthetic primer

<400> SEQUENCE: 5
caaacaaaca ttcaaatatc aatccaagga ggagctgctc aacatg                   46
```

<210> SEQ ID NO 6
<211> LENGTH: 23
<212> TYPE: DNA
<213> ORGANISM: Artificial Sequence
<220> FEATURE:
<223> OTHER INFORMATION: Synthetic primer

<400> SEQUENCE: 6
cactttgtga ccattccggt ttg                                            23

<210> SEQ ID NO 7
<211> LENGTH: 23
<212> TYPE: DNA
<213> ORGANISM: Artificial Sequence
<220> FEATURE:
<223> OTHER INFORMATION: Synthetic primer

<400> SEQUENCE: 7
cactttgtga ccattccggt ttg                                            23

<210> SEQ ID NO 8
<211> LENGTH: 70
<212> TYPE: DNA
<213> ORGANISM: Artificial Sequence
<220> FEATURE:
<223> OTHER INFORMATION: Synthetic primer

<400> SEQUENCE: 8
caaacaaaca ttcaaatatc aatcctctct attttgaatg tttgtttgca aggaggagct    60
gctgaagatg                                                           70

<210> SEQ ID NO 9
<211> LENGTH: 71
<212> TYPE: DNA
<213> ORGANISM: Artificial Sequence
<220> FEATURE:
<223> OTHER INFORMATION: Synthetic primer

<400> SEQUENCE: 9
caaacaaaca ttcaaatatc aatcctcaac tattttgaat gtttgtttgc aaggaggagc    60
tgctgaagat g                                                         71

<210> SEQ ID NO 10
<211> LENGTH: 43
<212> TYPE: DNA
<213> ORGANISM: Artificial Sequence
<220> FEATURE:
<223> OTHER INFORMATION: Synthetic primer

<400> SEQUENCE: 10
caattcaaat cacaataatc aatccttcct gagcccagag agc                      43

<210> SEQ ID NO 11
<211> LENGTH: 67
<212> TYPE: DNA
<213> ORGANISM: Artificial Sequence
<220> FEATURE:
<223> OTHER INFORMATION: Synthetic primer

<400> SEQUENCE: 11
caattcaaat cacaataatc aatcacactc cacacatgat ttgaattgct tcctgagccc    60
agagagc                                                              67

<210> SEQ ID NO 12

<210> SEQ ID NO 12
<211> LENGTH: 25
<212> TYPE: DNA
<213> ORGANISM: Artificial Sequence
<220> FEATURE:
<223> OTHER INFORMATION: Synthetic primer

<400> SEQUENCE: 12
gtcattgatc agtttggaga gtagg                                25

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
gattgattat tgtgatttga attg                                 24

<210> SEQ ID NO 14
<211> LENGTH: 18
<212> TYPE: DNA
<213> ORGANISM: Artificial Sequence
<220> FEATURE:
<223> OTHER INFORMATION: Synthetic primer

<400> SEQUENCE: 14
gtattccttg cctgtcca                                        18

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
tagttgcaaa tccgcgacaa                                      20

<210> SEQ ID NO 16
<211> LENGTH: 57
<212> TYPE: DNA
<213> ORGANISM: Artificial Sequence
<220> FEATURE:
<223> OTHER INFORMATION: Synthetic primer

<400> SEQUENCE: 16
atgatgatgt attgtagtta tgaaaggtat tgaagttttg tcgcggattt gcaacta    57

<210> SEQ ID NO 17
<211> LENGTH: 13
<212> TYPE: DNA
<213> ORGANISM: Artificial Sequence
<220> FEATURE:
<223> OTHER INFORMATION: Synthetic primer

<400> SEQUENCE: 17
aatacatcat cat                                             13

<210> SEQ ID NO 18
<211> LENGTH: 15
<212> TYPE: DNA
<213> ORGANISM: Artificial Sequence
<220> FEATURE:
<223> OTHER INFORMATION: Synthetic primer

<400> SEQUENCE: 18

```
acaatacatc atcat                                              15

<210> SEQ ID NO 19
<211> LENGTH: 55
<212> TYPE: DNA
<213> ORGANISM: Artificial Sequence
<220> FEATURE:
<223> OTHER INFORMATION: Synthetic primer

<400> SEQUENCE: 19
atgatgatgt attgtagtta tgaatacatc atcatttgtc gcggatttgc aacta    55

<210> SEQ ID NO 20
<211> LENGTH: 58
<212> TYPE: DNA
<213> ORGANISM: Artificial Sequence
<220> FEATURE:
<223> OTHER INFORMATION: Synthetic primer

<400> SEQUENCE: 20
atgatgatgt attgtagtta tgaacaatac atcatcattt gtcgcggatt tgcaacta   58

<210> SEQ ID NO 21
<211> LENGTH: 60
<212> TYPE: DNA
<213> ORGANISM: Artificial Sequence
<220> FEATURE:
<223> OTHER INFORMATION: Synthetic primer

<400> SEQUENCE: 21
atgatgatgt attgtagtta tgaatacaat acatcatcat ttgtcgcgga tttgcaacta  60

<210> SEQ ID NO 22
<211> LENGTH: 55
<212> TYPE: DNA
<213> ORGANISM: Artificial Sequence
<220> FEATURE:
<223> OTHER INFORMATION: Synthetic primer

<400> SEQUENCE: 22
atgatgatgt attgtagtta tgaatacatc atcatttgtc gcggatttgc aacta    55

<210> SEQ ID NO 23
<211> LENGTH: 24
<212> TYPE: DNA
<213> ORGANISM: Artificial Sequence
<220> FEATURE:
<223> OTHER INFORMATION: Synthetic primer

<400> SEQUENCE: 23
gattgatatt tgaatgtttg tttg                                    24

<210> SEQ ID NO 24
<211> LENGTH: 55
<212> TYPE: DNA
<213> ORGANISM: Artificial Sequence
<220> FEATURE:
<223> OTHER INFORMATION: Synthetic primer

<400> SEQUENCE: 24
caaacaaaca ttcaaatatc aatcaatgtt tgtttggctg cggtaggtgg ttcaa    55

<210> SEQ ID NO 25
<211> LENGTH: 13
<212> TYPE: DNA
```

```
<213> ORGANISM: Artificial Sequence
<220> FEATURE:
<223> OTHER INFORMATION: Synthetic primer

<400> SEQUENCE: 25
aatacatcat cat                                                     13

<210> SEQ ID NO 26
<211> LENGTH: 24
<212> TYPE: DNA
<213> ORGANISM: Artificial Sequence
<220> FEATURE:
<223> OTHER INFORMATION: Synthetic primer

<400> SEQUENCE: 26
gtttgtattt agatgaatag aaag                                         24

<210> SEQ ID NO 27
<211> LENGTH: 55
<212> TYPE: DNA
<213> ORGANISM: Artificial Sequence
<220> FEATURE:
<223> OTHER INFORMATION: Synthetic primer

<400> SEQUENCE: 27
ttacttcact ttctatttac aatcaagtga agtaaattgc gaaatttggt acagc        55

<210> SEQ ID NO 28
<211> LENGTH: 59
<212> TYPE: DNA
<213> ORGANISM: Artificial Sequence
<220> FEATURE:
<223> OTHER INFORMATION: Synthetic primer

<400> SEQUENCE: 28
atgatgatgt attgtagtta tgaatacatc atcatctgat tgcgccgaag tttacattc    59

<210> SEQ ID NO 29
<211> LENGTH: 64
<212> TYPE: DNA
<213> ORGANISM: Artificial Sequence
<220> FEATURE:
<223> OTHER INFORMATION: Synthetic primer

<400> SEQUENCE: 29
ctaattacta acatcactaa caatgttagt aattagttgt ttataacaac gaagggacta   60
acgt                                                               64

<210> SEQ ID NO 30
<211> LENGTH: 56
<212> TYPE: DNA
<213> ORGANISM: Artificial Sequence
<220> FEATURE:
<223> OTHER INFORMATION: Synthetic primer

<400> SEQUENCE: 30
atgatgatgt attgtagtta tgaatacatc atcatgattg cgtaatgcac cgtgtt       56

<210> SEQ ID NO 31
<211> LENGTH: 55
<212> TYPE: DNA
<213> ORGANISM: Artificial Sequence
<220> FEATURE:
<223> OTHER INFORMATION: Synthetic primer

<400> SEQUENCE: 31
```

```
caaacaaaca ttcaaatatc aatcaatgtt tgtttggctg cggtaggtgg ttcaa        55

<210> SEQ ID NO 32
<211> LENGTH: 55
<212> TYPE: DNA
<213> ORGANISM: Artificial Sequence
<220> FEATURE:
<223> OTHER INFORMATION: Synthetic primer

<400> SEQUENCE: 32
atgatgatgt attgtagtta tgaatacatc atcatttgtc gcggatttgc aacta        55

<210> SEQ ID NO 33
<211> LENGTH: 24
<212> TYPE: DNA
<213> ORGANISM: Artificial Sequence
<220> FEATURE:
<223> OTHER INFORMATION: Synthetic primer

<400> SEQUENCE: 33
gattgatatt tgaatgtttg tttg                                          24

<210> SEQ ID NO 34
<211> LENGTH: 24
<212> TYPE: DNA
<213> ORGANISM: Artificial Sequence
<220> FEATURE:
<223> OTHER INFORMATION: Synthetic primer

<400> SEQUENCE: 34
gattgtaaat agaaagtgaa gtaa                                          24

<210> SEQ ID NO 35
<211> LENGTH: 24
<212> TYPE: DNA
<213> ORGANISM: Artificial Sequence
<220> FEATURE:
<223> OTHER INFORMATION: Synthetic primer

<400> SEQUENCE: 35
attgttagtg atgttagtaa ttag                                          24

<210> SEQ ID NO 36
<211> LENGTH: 13
<212> TYPE: DNA
<213> ORGANISM: Artificial Sequence
<220> FEATURE:
<223> OTHER INFORMATION: Synthetic primer

<400> SEQUENCE: 36
aatacatcat cat                                                      13
```